Figure 2:
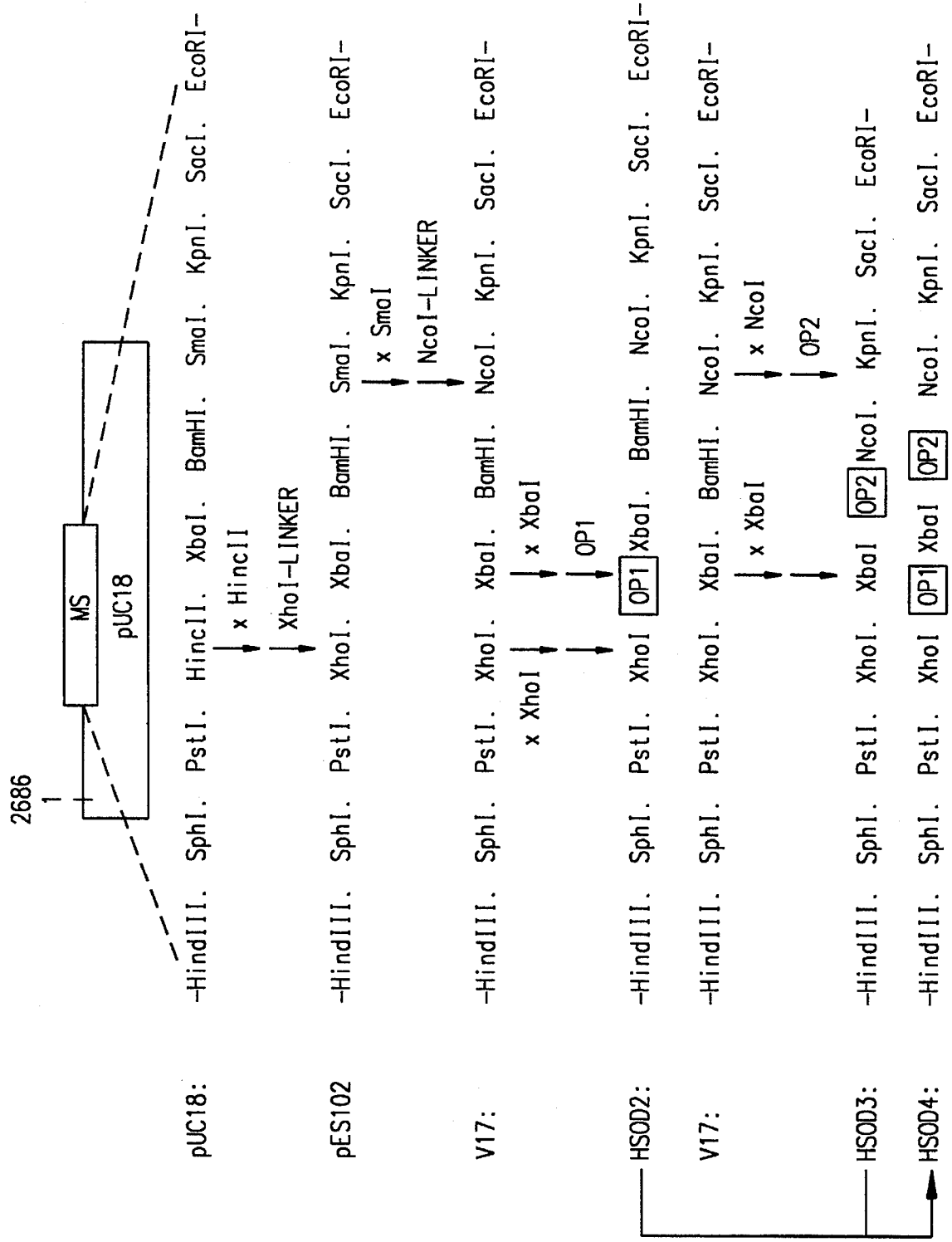

United States Patent [19]

Heckl et al.

[11] Patent Number: 5,589,371
[45] Date of Patent: *Dec. 31, 1996

[54] HUMAN MANGANESE SUPEROXIDE DISMUTASE (HMN-SOD)

[75] Inventors: Konrad Heckl, Heidelberg, Germany; Walter Spevak, Stockerau, Austria; Elinborg Ostermann, Wien, Austria; Andreas Zöphel, Neulengbach, Austria; Edeltraud Krystek, Wien, Austria; Ingrid Maurer-Fogy, Wien, Austria; Maria J. Wiche-Castanon, Wien, Austria; Christian Stratowa, Wien, Austria; Rudolf Hauptmann, Ebreichsdorf, Austria

[73] Assignee: Boehringer Ingelheim International GmbH, Germany

[*] Notice: The term of this patent shall not extend beyond the expiration date of Pat. No. 5,240,847.

[21] Appl. No.: 413,367

[22] Filed: Mar. 30, 1995

Related U.S. Application Data

[63] Continuation of Ser. No. 945,240, Sep. 15, 1992, Pat. No. 5,436,162, which is a continuation of Ser. No. 167,261, Mar. 11, 1988, Pat. No. 5,240,847.

[30] Foreign Application Priority Data

| May 26, 1900 | [DE] | Germany | 37 17 695.1 |
| Mar. 14, 1987 | [DE] | Germany | 37 08 306.6 |
| Jul. 10, 1987 | [DE] | Germany | 37 22 884.6 |
| Dec. 24, 1987 | [DE] | Germany | 37 44 038.1 |

[51] Int. Cl.$^6$ ................................. C12N 9/02
[52] U.S. Cl. .................. 435/189; 435/320.1; 435/254.2
[58] Field of Search ................................ 435/184, 320.1, 435/254.2

[56] References Cited

U.S. PATENT DOCUMENTS

| 3,920,521 | 11/1975 | Michelson et al. | 195/55 |
| 3,997,402 | 12/1976 | Michelson | 195/62 |
| 4,029,819 | 6/1977 | Michelson | 426/61 |
| 4,751,180 | 6/1988 | Cousens et al. | 435/68 |
| 5,066,591 | 11/1991 | Hallewell et al. | 435/189 |
| 5,115,097 | 5/1992 | Uda et al. | 530/326 |
| 5,196,335 | 3/1993 | Groner | 435/240.2 |
| 5,240,847 | 8/1993 | Heckl et al. | 435/189 |
| 5,246,847 | 9/1993 | Hartman et al. | 435/189 |
| 5,260,204 | 11/1993 | Heckl et al. | 435/189 |
| 5,270,195 | 12/1993 | Hartman et al. | 435/189 |
| 5,436,162 | 7/1995 | Heckl et al. | 435/320.1 |

FOREIGN PATENT DOCUMENTS

| 0138111 | 4/1985 | European Pat. Off. |
| 0172577 | 2/1986 | European Pat. Off. |
| 0284105 | 9/1988 | European Pat. Off. |
| 0284645 | 10/1988 | European Pat. Off. |
| 0303972 | 2/1989 | European Pat. Off. |
| 2417508 | 11/1974 | Germany . |
| 2183658 | 6/1987 | United Kingdom . |
| WO87/01387 | 3/1987 | WIPO . |

OTHER PUBLICATIONS

Bannister and Bannister, "Isolation and Characterization of Superoxide Dismutase", *Meth. Enzymol.* 105:88–93 (1984).
Barra et al., "Primary Structure of Mangano Superoxide Dismutase from Human Liver", *Oxyradicals and Their Scavenger Systems* 1:336–339 (1983).
Barra et al., "The Primary Structure of Human Liver Manganese Superoxide Dismutase", *J. Biol. Chem.* 259(20):12595–12601 (1984).
Beck et al., "Human Mn Superoxide Dismutase cDNA Sequence", *Nucl. Acids Res.* 15(21):9076 (1987).
Bialy, "Recombinant Proteins: Virtual Reality", *Bio/Technology* 5:883–890 (1987).
Bridges et al., "Distribution of Iron–Containing Superoxide Dismutase in Vascular Plants", *Plant Physiol.* 68:275–278 (1981).
English abstract for German Patent Document No. DE 2 417 508 (1974).
Heckl, K., "Isolation of cDNAs Encoding Human Manganese Superoxide Dismutase", *Nucl. Acids Res.* 16:6224 (1988).
Ho et al., "Isolation and Characterization of Complementary DNAs Encoding Human Manganese–Containing Superoxide Dismutase", *FEBS Letts.* 229(2):256–260 (1988).
Jabusch et al., "Some Sulfhydryl Properties and Primary Structure of Human Erythrocyte Superoxide Dismutase", *Biochemistry* 19:2310–2316 (1980).
Jay et al., "Gene Expression: Chemical Synthesis of E. coli Ribosome Binding Sites and Their Use in Directing the Expression of Mammalian Proteins in Bacteria", *Nucl. Acids Res.* 10:6319–6329 (1982).
Kozak, M., "Possible Role of Flanking Nucleotides in Recognition of the AUG Initiator Codon by Eukaryotic Ribosomes", *Nucl. Acids Res.* 9(20):5233–5252 (1981).
Kozak, M., "Analysis of Ribosome Binding Sites from the s1 Message of Reovirus", *J. Molec. Biol.* 156:807–820 (1982).
Lehninger, A. L., *Biochemistry, The Molecular Basis of Cell Structure and Function*, 2nd Ed., New York: Worth Publishers, p. 149 (1975).
Marres et al., "Nucleotide Sequence Analysis of Nuclear Gene Coding for Manganese Superoxide Dismutase of Yeast Mitochondria, a Gene Previously Assumed to Code for the Rieske Iron–Sulphur Protein", *Eur. J. Biochem.* 147:153–161 (1985).
Nakagawa et al., "Enzymatic Cleavage of Amino Terminal Methionine From Recombinant Human Interleukin 2 and Growth Hormone by Aminopeptidase M", *Bio/Technology* 5:824–827 (1987).

(List continued on next page.)

Primary Examiner—Charles L. Patterson, Jr.
Attorney, Agent, or Firm—Sterne, Kessler, Goldstein & Fox P.L.L.C.

[57] ABSTRACT

The present invention relates to a method of preparing human Mn-superoxide dismutase (hMn-SOD) by genetic engineering, the DNA sequences which code for this enzyme, suitable vectors which contain these DNA sequences and host cells which can express these DNA sequences, and the enzyme hMn-SOD itself. Suggestions as to the use of this enzyme are also described.

2 Claims, 15 Drawing Sheets

OTHER PUBLICATIONS

Sharp et al., "Codon Usage in Yeast: Cluster Analysis CLearly Differentiates Highly and Lowly Expressed Genes", *Nucl. Acids Res.* 14(13):5125–5143 (1986).

Touati, D., "Cloning and Mapping of the Manganese Superoxide Dismutase Gene(sodA) of *Escherichia coli* K–12", *J. Bacteriol.* 155(3):1078–1087 (1983).

Urdea, M. S., et al., "Chemical Synthesis of a Gene for Human Epidermal Growth Factor Urogastrone and its Expression in Yeast", *Proc. Natl. Acad. Sci. USA* 80(24):7461–7465 (1983).

GAATTCGCATGGTCGACTAC

```
    I   M   Q   L   H   H   S   K   H   H   A   A   Y
GATCATGCAGCTGCACCACAGCAAGCACCACGCGGCCTAC

V   N   N   L   N   V   T   E   E   K   Y   Q   E   A
GTGAACAACCTGAACGTCACCGAGGAGAAGTACCAGGAGGCG

L   A   K   G   D   V   T   A   Q   I   A   L   Q   P   A   L
TTGGCCAAGGGAGATGTTACAGCCCAGATAGCTCTTCAGCCTGCACTG

K   F   N   G   G   H   I   N   H   S   I   F   W   T   N
AAGTTCAATGGTGGTGGTCATATCAATCATAGCATTTCTGGACAAAC

L   S   P   N   G   G   E   P   K   G   E   L   L   E   A
CTCAGCCCTAACGGTGGTGGAGAACCCAAAGGGGAGTTGCTGGAAGCC

I   K   R   D   F   G   S   F   D   K   F   K   E   K   L   T
ATCAAACGTGACTTTGGTTCCTTTGACAAGTTTAAGGAGAAGCTGACG

A   A   S   V   G   V   Q   G   S   G   W   G   W   L   G   F
GCTGCATCTGTTGGTGTCCAAGGCTCAGGTTGGGGTTGGCTTGGTTTC

N   K   E   R   G   H   L   Q   I   A   A   C   P   N   Q   D
AATAAGGAACGGGGACACTTACAAATTGCTGCTTGTCCAAATCAGGAT

P   L   Q   G   T   T   G   L   I   P   L   L   G   I   D   V
CCACTGCAAGGAACAACAGGCCTTATTCCACTGCTGGGGATTGATGTG

W   E   H   A   Y   Y   L   Q   Y   K   N   V   R   P   D   Y
TGGGAGCACGCTTACTACCTTCAGTATAAAAATGTCAGGCCTGATTAT

L   K   A   I   W   N   V   I   N   W   E   N   V   T   E   R
CTAAAAGCTATTTGGAATGTAATCAACTGGGAGAATGTAACTGAAAGA

Y   M   A   C   K   K   *
TACATGGCTTGCAAAAAGTAAACCACGATCGTTATGCTGAAAAAAAAA

AAAAAAAAAAAAAAAAAAAAAGTAGTCGACCATGCGAATTC
```

FIG. 1

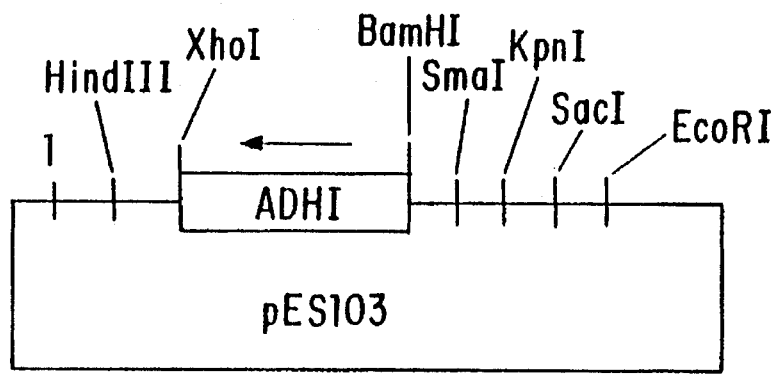
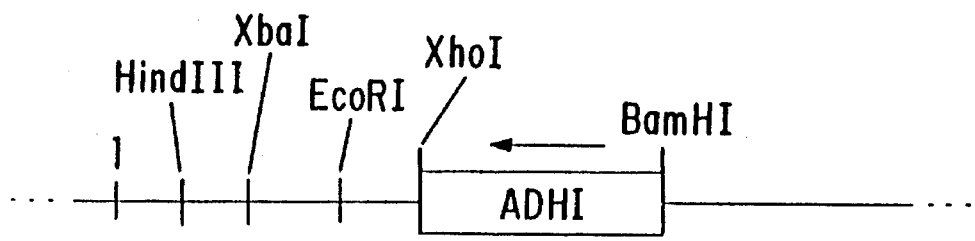
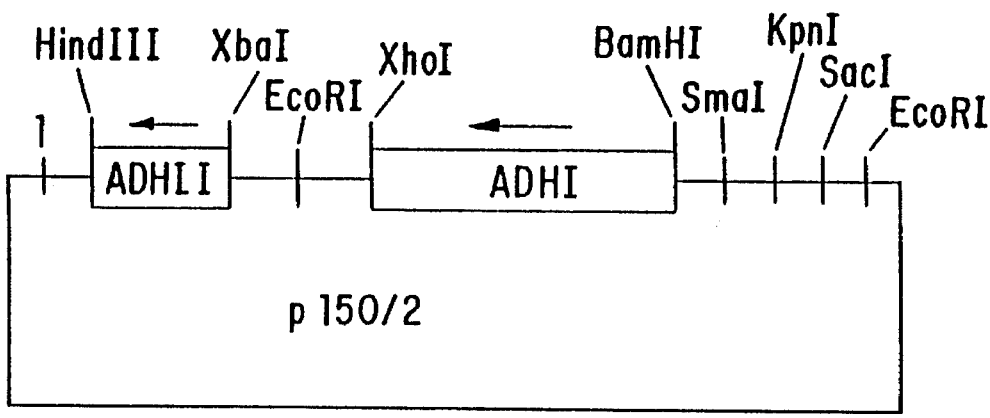
FIG. 7

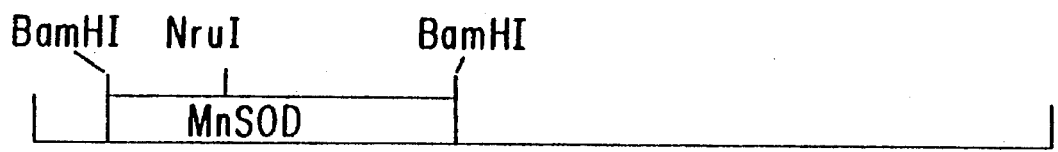
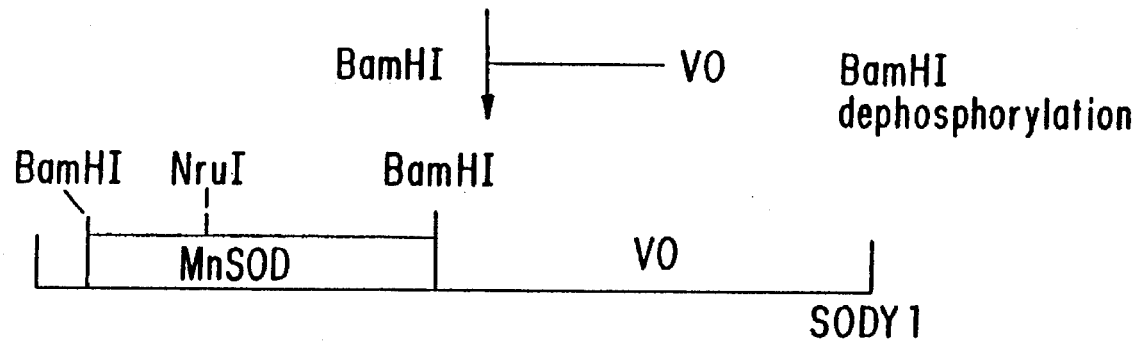
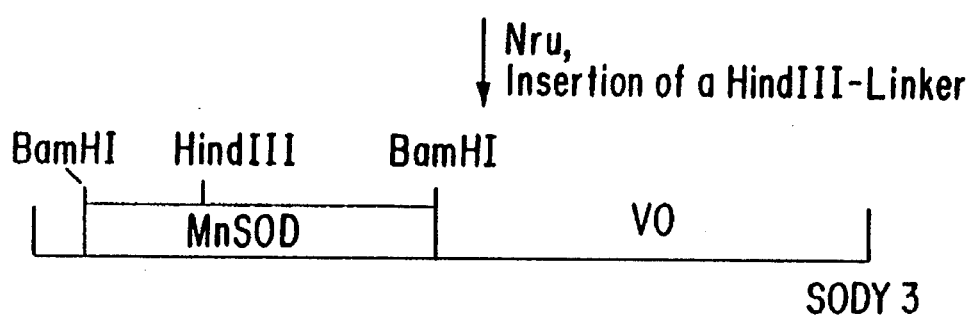
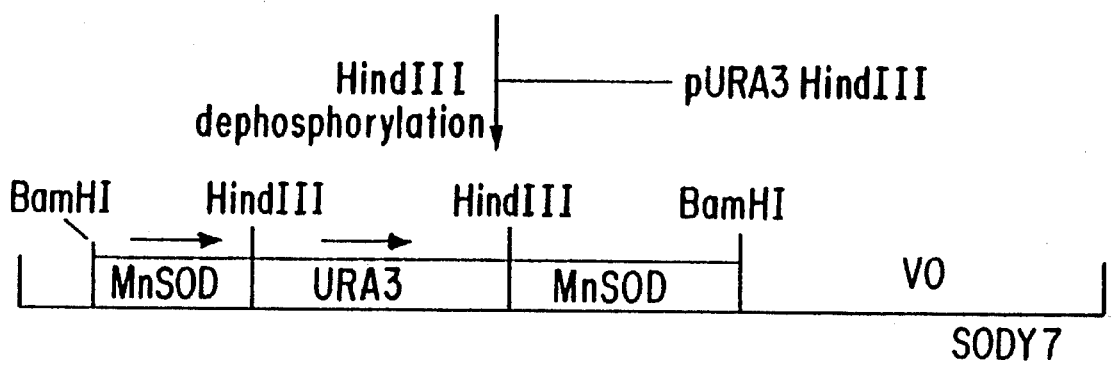
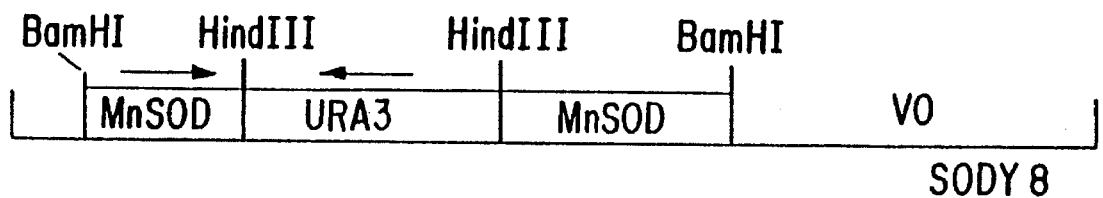
FIG. 10

HUMAN MANGANESE SUPEROXIDE DISMUTASE (HMN-SOD)

This application is a continuation of application Ser. No. 07/945,240, filed Sep. 15, 1992, issued on Jul. 25, 1995 as U.S. Pat. No. 5,436,162, application Ser. No. 07/945,240, which is continuation of application Ser. No. 07/167,261, filed Mar. 11, 1988, which issued on Aug. 31, 1993 as U.S. Pat. No. 5,240,847.

The present invention relates to a method of producing human Mn-superoxide dismutase (hMn-SOD) by genetic engineering, the DNA sequences which code for this enzyme, suitable vectors which contain these DNA sequences and host cells which are capable of expressing these DNA sequences, and the enzyme hMn-SOD itself. Suggestions for the use of this enzyme are also described.

As a consequence of various biochemical processes in biological systems (e.g. redox processes in the respiratory chain, oxidation in the cytoplasm), $O_2^-$ radicals are continuously formed, as is well known, these radicals being highly cytotoxic and capable of resulting in tissue damage. The degradation of collagen and synovial fluid by such radicals has been discussed with reference to pathological situations, e.g. in the course of rheumatically caused diseases (Pasquier, C. et al., Inflammation 8, 27–32, 1984). Eukaryotic cells contain two forms of superoxide dismutases, one of which occurs predominantly in cytosol (Cu/Zn-SOD) whilst the other occurs primarily in the mitochondria (Mn-SOD). In liver mitochondria it has been found that Mn enzyme is localised in the matrix enclosing the inner membrane, although Mn-SOD has also been detected in the cytosol of the liver cells (Mc Cord J. M. et al., In: Superoxide and Superoxide Dismutases (A. M. Michelson, J. M. Mc Cord, I. Fridovich, eds.) Academic Press, New York, 129–138, 1977).

In prokaryotes there is an Fe-SOD as well as an Mn-SOD. The former has also been found in algae and protozoa as well as in some plant species (Bridges, S. M., Salin, M. L., Plant Physiol. 68, 275–278, 1981). These highly active enzymes catalyse the disproportionation $O_2^- + O_2^- + 2H^+ \rightarrow H_2O_2 + O_2$ and prevent, by this dismutation of the superoxide radicals, the concentration thereof and hence their damaging effect on cells. Apart from the endoplasmic reticulum of the liver, the mitochondrial membranes can be regarded as one of the most important sites of $O_2^-$ formation in animal cells, so that it is not surprising that mitochondria have their own special SOD(Mn-SOD) available.

The structural gene of a prokaryotic Mn-SOD (*E. coli*) was cloned and the chromosomal sodA gene was located (Touati, D., J. Bact. 155, 1078–1087, 1983).

The 699 bp long nucleotide sequence of a mitochondrial yeast Mn-SOD was determined and the primary structure of both the precursor and also the mature protein was derived therefrom—with molecular weight of 26123 Da for the precursor and 23059 Da for the mature protein (Marres, C.A.M. et al., Eur. J. Biochem. 147, 153–161 (1985). Thus, the Mn- and Cu/Zn-SOD (MW=14893, EP-A 138111) differ significantly in their molecular weights.

The complete amino acid sequence of Mn-SOD from human liver was published by D. Barra, and according to this publication the hMn-SOD is supposed to consist of 196 amino acids (Barra, D. et al., J. Biol. Chem. 259, 12595–12601, 1984). Human Cu/Zn-SOD from erythrocytes, on the other hand, consists of 153 amino acids (Jabusch, J. R., et al., Biochemistry 19, 2310–2316, 1980) and shows no sequence homologies with hMn-SOD) (Barra. D. et al., see above).

Generally, the superoxide dismutases are credited with a protective function against certain inflammatory processes. In particular, deficiency in Mn-SOD is supposed to have some significance in the development of rheumatoid arthritis (Pasquier, C. et al., see above). SOD is also assumed to have a protective effect against alcohol-induced liver damage (Del Villano B.C. et al., Science 207, 991–993, 1980).

The cloning and expression of a human SOD is known only for human Cu/Zn-SOD from human liver (EP-A 138111).

In view of the above-mentioned essential properties of the superoxide dismutases, particularly hMn-SOD, a demand for its use in therapy and/or diagnosis can be expected. For this purpose it is advantageous to have access to sufficient quantities of Mn-SOD of the same species, i.e. human, in homogeneous form. The projected aim which derives therefrom is to minimise or prevent the immunological reactions which can be expected, e.g. after therapeutic use.

Only with the development of technologies for the recombination of foreign DNA with vector DNA and the possibility of establishing the former in stable form in microorganisms and expressing it therein has made it possible to produce homogeneous proteins of animal or human origin in large quantities. The objective here is different, namely that the enzyme thus prepared, hMn-SOD, should have a biological activity spectrum which is characteristic of authentic genuine hMn-SOD.

An aim of the present invention was therefore to discover or produce the DNA sequence coding for this enzyme, for the first time, using genetic engineering, and to indicate for the first time the methods by which this sequence can be obtained.

According to the invention this problem is solved by searching through a cDNA gene bank obtained from human cells of placental origin with synthetically produced DNA probe molecules, thereby isolating the gene which codes for hMn-SOD. In order to obtain the gene for hMn-SOD, the mRNA can be isolated, by known methods, from cells which produce the desired enzyme. Various starting materials may be used, e.g. metabolically active gland tissue such as liver or placenta. After production of the cDNA, which can be obtained by known methods by primed synthesis with reverse transcriptase using isolated mRNA, subsequent incorporation into a suitable vector and amplification to obtain a complete cDNA gene bank, the latter can be searched with a defined, radioactively labelled DNA probe or a mixture of various probes of this kind. In order to take account of the degeneracy of the genetic code, defined DNA probe mixtures are preferably used which represent all possible nucleotide variations for one and the same amino acid or which are selected so that the number of DNA probes of a mixture to be synthesised is as small as possible and the homology with the hMn-SOD DNA sequence sought is as high as possible. Another criterion for selection in the synthesis of DNA probes may require that these probes are complementary to at least two independent regions, for example near the 3' and 5' ends of the putative gene sequence. In this way, clones which show positive signals against, for example, both independent DNA probes can be identified by means of at least two separate hybridisations. These clones may then preferably be used to isolate the hMn-SOD gene, since they can be expected to contain either a substantial part of or the complete gene for hMn-SOD.

The particular DNA sequences used for the DNA probes according to the invention were derived from liver tissue using the amino acid sequence of human Mn-SOD published by D. Barra et al. (Barra, D. et al., Oxy Radicals and their scavenger Systems, Vol. 1, 336–339, 1983). In particular, two regions of the putative hMn-SOD DNA sequence which code for at least five amino acid groups, preferably for 8 amino acid groups, may preferably be used, a DNA probe length of at least 14, preferably 23 bases being advantageous. It is particularly advantageous if a DNA probe is complementary to the derived hMn-SOD DNA sequence the genetic information of which is colinear with the amino acid groups 39 to 46 and a second DNA probe is complementary to the corresponding DNA region which codes for amino acid groups 200 to 207 of the known amino acid sequence. Similarly, of course, DNA sequences which may be derived using other Mn-superoxide dismutases may also be used as probes.

Using a DNA probe of this kind it is possible to obtain positive clones from which a cDNA sequence corresponding to the following formula Ia may be isolated, containing a large amount of a region coding for hMn-SOD:

---

Formula Ia

---

G ATC ATG CAG CTG CAC CAC AGC AAG CAC CAC GCG GCC TAC
GTG AAC AAC CTG AAC GTC ACC GAG GAG AAG TAC CAG GAG
GCG TTG GCC AAG GGA GAT GTT ACA GCC CAG ATA GCT CTT
CAG CCT GCA CTG AAG TTC AAT GGT GGT GGT CAT ATC AAT
CAT AGC ATT TTC TGG ACA AAC CTC AGC CCT AAC GGT GGT
GGA GAA CCC AAA GGG GAG TTG CTG GAA GCC ATC AAA CGT
GAC TTT GGT TCC TTT GAC AAG TTT AAG GAG AAG CTG ACG
GCT GCA TCT GTT GGT GTC CAA GGC TCA GGT TGG GGT TGG
CTT GGT TTC AAT AAG GAA CGG GGA CAC TTA CAA ATT GCT
GCT TGT CCA AAT CAG GAT CCA CTG CAA GGA ACA ACA GGC
CTT ATT CCA CTG CTG GGG ATT GAT GTG TGG GAG CAC GCT
TAC TAC CTT CAG TAT AAA AAT GTC AGG CCT GAT TAT CTA
AAA GCT ATT TGG AAT GTA ATC AAC TGG GAG AAT GTA ACT
GAA AGA TAC ATG GCT TGC AAA AAG TAA

---

Surprisingly, it has now been found that the cDNA found codes for an amino acid sequence which differs from the published amino acid sequence (Barra, D. et al., J. Biol.Chem. 259, 12595–12601, 1984) in some of the groups and in their length from one another. The differences discovered in this sequence from the "Barra sequence" are concerned with the amino acid positions 42, 88, 109 and 131 (in each case Glu instead of Gln) and two additional amino acids Gly and Trp between positions 123 and 124, so that the DNA sequence according to the invention corresponds to an hMn-SOD of 198 amino acids.

It was also completely unexpected that, on the other hand, a cDNA coding for hMn-SOD could be isolated which indicates an amino acid substitution at position 29 (codon for Gln instead of Lys) and thus in this point has an additional difference from "the Barra sequence" and from formula Ia, corresponding to formula Ib:

If one assumes that the Barra sequence was correctly analysed, using the nucleotide or amino acid sequence according to the invention the possibility has to be considered that for the first time, and surprisingly, this indicates the possible existence of different genes or their allelic manifestations or isoenzymes for hMn-SOD.

Since it is possible to obtain cDNA-bearing clones which lack the end required for the complete hMn-SOD gene, another object of the present invention was to prepare the complete gene for hMn-SOD.

This aim can be achieved by various known strategies. For example, the sequence obtained may itself be used as a DNA probe and the cDNA bank can be searched once more with it in order to detect a complete gene or a cDNA with the missing end or the DNA sequence obtained may be used as a hybridisation probe against a genomic bank in order to isolate the complete hMn-SOD gene after identifying it.

Alternatively, there is the possibility of synthesising oligonucleotides in which the nucleotide sequence corresponds to the missing end of the hMn-SOD and obtaining the complete cDNA for hMn-SOD with the aid of these oligonucleotides, after suitable linker ligation. This method has the advantage that, for example, a DNA coding for hMn-SOD may be obtained in which the 5' end begins directly with the start codon (ATG).

---

Formula Ib

---

CAC CAC AGC CAG CAC CAC GCG GCC TAC GTG AAC AAC CTG AAC
GTC ACC GAG GAG AAG TAC CAG GAG GCG TTG GCC AAG GGA GAT
GTT ACA GCC CAG ATA GCT CTT CAG CCT GCA CTG AAG TTC AAT
GGT GGT GGT CAT ATC AAT CAT AGC ATT TTC TGG ACA AAC CTC
AGC CCT AAC GGT GGT GGA GAA CCC AAA GGG GAG TTG CTG GAA
GCC ATC AAA CGT GAC TTT GGT TCC TTT GAC AAG TTT AAG GAG
AAG CTG ACG GCT GCA TCT GTT GGT GTC CAA GGC TCA GGT TGG
GGT TGG CTT GGT TTC AAT AAG GAA CGG GGA CAC TTA CAA ATT
GCT GCT TGT CCA AAT CAG GAT CCA CTG CAA GGA ACA ACA GGC
CTT ATT CCA CTG CTG GGG ATT GAT GTG TGG GAG CAC GCT TAC
TAC CTT CAG TAT AAA AAT GTC AGG CCT GAT TAT CTA AAA GCT
ATT TGG AAT GTA ATC AAC TGG GAG AAT GTA ACT GAA AGA TAC
ATG GCT TGC AAA AAG TAA

The DNA sequence of formula II has been found to be particularly suitable for solving this problem, completing the cDNAs according to the invention which code, for example, from amino acid 22 or 26, this sequence beginning with the 5' start codon ATG and ending with the codon for amino acid 31 (His, whilst AAG [Lys]=1), on the basis of the known codon preferences such as those which apply to yeast (Sharp, P.M. et al., Nucl.Acids.Res. 14 (13), 5125–5143, 1986)

| Formula II |
|---|
| 5' ATG AAG CAC TCT TTG CCA GAC TTG CCA TAC GAC TAC GGT GCT<br>TAC TTC GTG AGA AAC GGT CTG AAG GGT ATG CTG ATG CCA CGA<br>CTA GAA CCA CAC ATC AAT GCT CAA ATC ATG CAA TTG CAC CAC<br>GAT CTT GGT GTG TAG TTG CGA GTT TAG TAC GTT AAC GTG GTG<br>TCT AAG CAC CAT G<br>AGA TTC GTG GTA C |

Similarly, other known synonymous codons may be used to complete the hMn-SOD gene or to synthesise the entire gene in vitro, e.g. those which facilitate an optimum codon-anticodon alternation in bacteria, e.g. *E. coli*, and increase the efficiency of translation (Grosjean, H., Fiers, W., Gene 18, 199–209, 1982; Ikemura, T., J. Mol. Biol. 151, 389–409, 1981) or codons which correspond to the actual conditions in mammalian cells (Grantham, R. et al., Nucleic Acid Research 9, 43–47, 1981). The latter may preferably be used for transformation and subsequently for expression in mammalian cells.

It is theoretically possible to split off the methionine group which is coded by the start codon ATG and which precedes the mature hMn-SOD, beginning with the first amino acid lysine, using methods known per se, for example using CNBr or CNCl. However, since other internal methionine groups may occur, e.g. at positions 23 or 192, in the mature enzyme hMn-SOD, such a procedure is impracticable, with the result that in this case the additional N-terminal methionine group remains, without affecting the biological activity of hMn-SOD.

However, enzymatic cleaving may also be envisaged, in which suitable synthetic linkers may be used in known manner, since codons for corresponding specific amino acids can be expected to be located at the desired positions on the vector which contains the hMn-SOD cDNA. For example, Arg or Lys groups for a tryptic cleavage or codons which code for protease-sensitive amino acids will generally be used. These may be positioned in front of or behind the start codon or within the coding region.

An additional aim of this invention was to express the sequence coding for hMn-SOD in suitable host cells for the first time by genetic engineering, to produce the homogeneous enzyme hMn-SOD by such methods for the first time, to isolate it and prepare it in pure form and to describe for the first time the procedure required for this.

According to the invention, this aim was achieved by inserting the DNA sequences coding for hMn-SOD, for example of formula IIIa or IIIb

| Formula IIIa |
|---|
| 5' ATG AAG CAC TCT TTG CCA GAC TTG CCA TAC GAC TAC GGT<br>CCT CTA GAA CCA CAC ATC AAT GCT CAA ATC ATG CAA TTG<br>CAC CAC TCT AAG CAC CAC GCG GCC TAC GTG AAC AAC CTG<br>AAC GTC ACC GAG GAG AAG TAC CAG GAG GCG TTG GCC AAG<br>GGA GAT GTT ACA GCC CAG ATA GCT CTT CAG CCT GCA CTG<br>AAG TTC AAT GGT GGT GGT CAT ATC AAT CAT AGC ATT TTC<br>TGG ACA AAC CTC AGC CCT AAC GGT GGT GGA GAA CCC AAA<br>GGG GAG TTG CTG GAA GCC ATC AAA CGT GAC TTT GGT TCC<br>TTT GAC AAG TTT AAG GAG AAG CTG ACG GCT GCA TCT GTT<br>GGT GTC CAA GGC TCA GGT TGG GGT TGG CTT GGT TTC AAT<br>AAG GAA CGG GGA CAC TTA CAA ATT GCT GCT TGT CCA AAT<br>CAG GAT CCA CTG CAA GGA ACA ACA GGC CTT ATT CCA CTG<br>CTG GGG ATT GAT GTG TGG GAG CAC GCT TAC TAC CTT CAG<br>TAT AAA AAT GTC AGG CCT GAT TAT CTA AAA GCT ATT TGG<br>AAT GTA ATC AAC TGG GAG AAT GTA ACT GAA AGA TAC ATG<br>GCT TGC AAA AAG TAA |
| Formula IIIb |
| 5' ATG AAG CAC TCT TTG CCA GAC TTG CCA TAC GAC TAC GGT<br>GCT CTA GAA CCA CAC ATC AAT GCT CAA ATC ATG CAA TTG<br>CAC CAC TCT CAG CAC CAC GCG GCC TAC GTG AAC AAC CTG<br>AAC GTC ACC GAG GAG AAG TAC CAG GAG GCG TTG GCC AAG<br>GGA GAT GTT ACA GCC CAG ATA GCT CTT CAG CCT GCA CTG<br>AAG TTC AAT GGT GGT GGT CAT ATC AAT CAT AGC ATT TTC<br>TGG ACA AAC CTC AGC CCT AAC GGT GGT GGA GAA CCC AAA<br>GGG GAG TTG CTG GAA GCC ATC AAA CGT GAC TTT GGT TCC<br>TTT GAC AAG TTT AAG GAG AAG CTG ACG GCT GCA TCT GTT<br>GGT GTC CAA GGC TCA GGT TGG GGT TGG CTT GGT TTC AAT<br>AAG GAA CGG GGA CAC TTA CAA ATT GCT GCT TGT CCA AAT<br>CAG GAT CCA CTG CAA GGA ACA ACA GGC CTT ATT CCA CTG |

```
CTG GGG ATT GAT GTG TGG GAG CAC GCT TAC TAC CTT CAG
TAT AAA AAT GTC AGG CCT GAT TAT CTA AAA GCT ATT TGG
AAT GTA ATC AAC TGG GAG AAT GTA ACT GAA AGA TAC ATG
GCT TGC AAA AAG TAA
``` optionally provided with corresponding signal or control sequences, into suitable vectors and transforming suitable host cells therewith. After cultivation of the transformed host cells the polypeptides formed are isolated and purified by methods known per se. The polypeptides obtained correspond to the following formulae IVa and IVb.

particularly in *E. coli* or *S. cerevisiae*. The problem of glycosylation in yeast, for example, can be avoided by using mutants which are deficient in the glycosylation of proteins (alg mutants) (e.g. Huffaker, T. C., Robbins P. W., Proc. Natl. Acad. Sci. USA 80, 7466–7470, 1987).

Formula IVa

| 1 | 5 | 10 | 15 |
|---|---|---|---|
| Lys His Ser Leu | Pro Asp Leu Pro Tyr | Asp Tyr Gly Ala Leu | Glu |
| | 20 | 25 | 30 |
| Pro His Ile Asn | Ala Gln Ile Met Gln | Leu His His Ser Lys | His |
| | 35 | 40 | 45 |
| His Ala Ala Tyr | Val Asn Asn Leu Asn | Val Thr Glu Glu Lys | Tyr |
| | 50 | 55 | 60 |
| Gln Glu Ala Leu | Ala Lys Gly Asp Val | Thr Ala Gln Ile Ala | Leu |
| | 65 | 70 | 75 |
| Gln Pro Ala Leu | Lys Phe Asn Gly Gly | Gly His Ile Asn His | Ser |
| | 80 | 85 | 90 |
| Ile Phe Trp Thr | Asn Leu Ser Pro Asn | Gly Gly Gly Glu Pro | Lys |
| | 95 | 100 | 105 |
| Gly Glu Leu Leu | Glu Ala Ile Lys Arg | Asp Phe Gly Ser Phe | Asp |
| | 110 | 115 | 120 |
| Lys Phe Lys Glu | Lys Leu Thr Ala Ala | Ser Val Gly Val Gln | Gly |
| | 125 | 130 | 135 |
| Ser Gly Trp Gly | Trp Leu Gly Phe Asn | Lys Glu Arg Gly His | Leu |
| | 140 | 145 | 150 |
| Gln Ile Ala Ala | Cys Pro Asn Gln Asp | Pro Leu Gln Gly Thr | Thr |
| | 155 | 160 | 165 |
| Gly Leu Ile Pro | Leu Leu Gly Ile Asp | Val Trp Glu His Ala | Tyr |
| | 170 | 175 | 180 |
| Tyr Leu Gln Tyr | Lys Asn Val Arg Pro | Asp Tyr Leu Lys Ala | Ile |
| | 185 | 190 | 195 |
| Trp Asn Val Ile Cys Lys Lys | Asn Trp Glu Asn Val | Thr Glu Arg Tyr Met | Ala |

Formula IVb

| 1 | 5 | 10 | 15 |
|---|---|---|---|
| Lys His Ser Leu | Pro Asp Leu Pro Tyr | Asp Tyr Gly Ala Leu | Glu |
| | 20 | 25 | 30 |
| Pro His Ile Asn | Ala Gln Ile Met Gln | Leu His His Ser Gln | His |
| | 35 | 40 | 45 |
| His Ala Ala Tyr | Val Asn Asn Leu Asn | Val Thr Glu Glu Lys | Tyr |
| | 50 | 55 | 60 |
| Gln Glu Ala Leu | Ala Lys Gly Asp Val | Thr Ala Gln Ile Ala | Leu |
| | 65 | 70 | 75 |
| Gln Pro Ala Leu | Lys Phe Asn Gly Gly | Gly His Ile Asn His | Ser |
| | 80 | 85 | 90 |
| Ile Phe Trp Thr | Asn Leu Ser Pro Asn | Gly Gly Gly Glu Pro | Lys |
| | 95 | 100 | 105 |
| Gly Glu Leu Leu | Glu Ala Ile Lys Arg | Asp Phe Gly Ser Phe | Asp |
| | 110 | 115 | 120 |
| Lys Phe Lys Glu | Lys Leu Thr Ala Ala | Ser Val Gly Val Gln | Gly |
| | 125 | 130 | 135 |
| Ser Gly Trp Gly | Trp Leu Gly Phe Asn | Lys Glu Arg Gly His | Leu |
| | 140 | 145 | 150 |
| Gln Ile Ala Ala | Cys Pro Asn Gln Asp | Pro Leu Gln Gly Thr | Thr |
| | 155 | 160 | 165 |
| Gly Leu Ile Pro | Leu Leu Gly Ile Asp | Val Trp Glu His Ala | Tyr |
| | 170 | 175 | 180 |
| Tyr Leu Gln Tyr | Lys Asn Val Arg Pro | Asp Tyr Leu Lys Ala | Ile |
| | 185 | 190 | 195 |
| Trp Asn Val Ile Cys Lys Lys | Asn Trp Glu Asn Val | Thr Glu Arg Tyr Met | Ala |

The sequences shown in formulae IIIa and IIIb are particularly suitable for the preparation of non-glycosylated hMn-SOD of formulae IVa and IVb in microorganisms, If necessary or advisable, the complete hMn-SOD gene, for example according to formula IIIa or IIIb, may be preceded by a leader or signal sequence directly before the first codon of the first N-terminal amino acid of the mature hMn-SOD or before the start codon ATG. This ensures that the hMn-SOD can be transported from the host cell and readily isolated from the culture medium.

Signal sequences of this kind have been described; they code for a generally hydrophobic protein content, which is split off by post-translational modification processes in the host cell (Davis, D. B., Tai, P.-C., Nature 283, 433–438, 1980; Perlman, D., Halvorson, H. O., J.Mol. Biol. 167, 391–409, 1983). If an ATG codon has been constructed in front of the first amino acid of the hMn-SOD, a gene product may be obtained which contains an N-terminal methionine in front of the lysine. The use of signal sequences of prokaryotes in order to secrete proteins into the periplasma and process them correctly is known (see Davis, B. D., Tai, P.-C., 1980).

Obviously, after isolating and cloning the hMn-SOD DNA sequence, it is possible specifically to modify the enzyme coded by this sequence. Enzyme modifications may be effected, for example, by controlled in vitro mutations with synthetic oligonucleotides, thereby influencing the catalytic properties of hMn-SOD and obtaining new enzymatic activities. The basic procedural steps for performing these protein manipulations are known (e.g. Winter, G. et al, Nature 29, 756–758 1982; Dalbadie-McFarland, G. et al. Proc. Natl. Acad. Sci. USA, 79, 6409–6313, 1982).

For the cloning, i.e. amplification and preparation, of the hMn-SOD gene it is possible to use *E. coli*, preferably *E. coli* C600 (Nelson et al. Virology 108, 338–350, 1981) or JM 101, or *E. coli* strains with at least one of the known sup-genotypes. However, the cloning may also be carried out in the gram-positive bacteria such as *B. subtilis*. Systems of this kind have been described many times.

Suitable hosts for the expression of the hMn-SOD gene according to the invention include both micro-organisms and also cultures of multicellular organisms. The term microorganisms includes prokaryotes, i.e. gram-negative or gram-positive bacteria and eukaryotes such as protozoa, algae, fungi or higher Protista. Of the gram-negative bacteria, the Enterobacteriaceae, for example *E. coli* are preferred hosts, whilst of the gram-positive bacteria the Bacillaceae and apathogenic Micrococcaceae, e.g. *B. subtilis* and *Staph. carnosus* are preferred hosts, and of the eukaryotes the Ascomycetes, particularly the yeasts, e.g. *Saccharomyces cerevisiae* are preferred hosts.

For single-cell microorganisms there are a plurality of starting vectors available which may be of both plasmidic and vital origin. These vectors may occur in a single copy or as multicopy vectors. Vectors of this kind which are suitable for the cloning and expression of the hMn-SOD according to the invention and for eukaryotic DNA sequences in general have been described in a number of publications and manuals (e.g. Maniatis, T. et al., Molecular Cloning, Cold Spring Harbor Laboratory, 1982; Glover, D. M. (ed.) DNA Cloning Vol. I, II, 1985) and are commercially obtainable.

In general, plasmid vectors which as a rule contain a replication origin and control sequences for transcription, translation and expression may be used in conjunction with these hosts. These sequences must originate from species which are compatible with the host cells. The vector usually carries, in addition to a replication site, recognition sequences which make it possible to phenotypically select the transformed cells. The selection may be carried out either by complementation, suppression or by deactivation of a marker. With regard to the first two methods, there are auxotrophic mutants of bacteria and yeast which are deficient in an essential product of metabolism, or nonsense mutants in which chain breakage occurs on translation of the gene in question. Various suppressor genes, e.g. supD, E, F (which suppress UAG), supC, G (which suppress UAG or UAA), are already known. In the third process, the vector carries a resistance gene against one or more cytotoxic agents, such as antibiotics, heavy metals. The insertion foreign DNA into a marker gene of this kind deactivates the latter so that the newly formed phenotype can be distinguished from the original phenotype.

For example, *E. coli* can be transformed with pBR322, a plasmid which originates from *E. coli* species (Bolivar, et al., Gene 2, 95 (1977). pBR322 contains genes for ampicillin and tetracycline resistance and thus provides simple means of identifying transformed cells, by converting the phenotype $Ap^r$, $Tc^r$ into $Ap^s$, $Tc^r$ by cloning in, for example, the PstI site in the β-lactamase gene. Other methods may equally be used, for which, for example, the lacZ-gene deactivation in λ and M 13 vectors and in various plasmids (e.g. pUC, pUR) is important. These very versatile selection systems have long been known and accordingly there is a wide range of literature on this subject.

In addition to selection markers of this kind, these vectors, particularly expression vectors, must contain signal sequences which ensure correct initiation and termination of the transcription. For the correct transcription of the hMn-SOD gene, therefore, these vectors may contain a bacterial or eukaryotic transcription unit consisting of a promoter, the coding region with the hMn-SOD gene and the adjoining terminator. Depending on the nature of the transcription units, these may contain conserved prototype sequences such as, for example, Pribnow-box or TTG sequence or CAAT-box, TATA-box, the known termination signals (for example AATAAA, TATGT), and at least one stop codon, whilst preferably promoters and terminators which are homologous with respect to the host are used. The mRNA formed usually contains a 3'poly(A) sequence and/or a 5' cap structure. Translation of the hMn-SOD gene requires a ribosomal binding site (RBS) consisting of a Shine/Dalgarno (S/D) sequence and an initiation codon at a defined spacing therefrom, generally of 3 to 12 nucleotides, and at least one stop codon. Alternatively, RBSs may be prepared synthetically, thereby increasing the homology with the 3' end of the 16S rRNA (Jay, E. et al. Nucleic Acids Res. 10, 6319–6329, 1982).

In eukaryotic expression systems, in particular, (for example *S. cerevisiae*), it is preferable to use regulatory systems for the translation which originate from the host, since in yeasts the conditions are analogous to those which apply to prokaryotes (homology of the S/D sequence with the 3' end of the 16S rRNA) and the signals or the RBS for initiating the translation are defined in a different way than in prokaryotes (e.g. Kozak, M., Nucleic Acids Res. 9, 5233–5252, 1981; Kozak, M., J. Mol. Biol. 156, 807–820, 1982).

Preferably, the cloning or expression vector has only one restriction endonuclease recognition site which either is present in the starting vector from the outset or can be inserted subsequently by means of suitable linkers. Linkers may either be obtained by a simple chemical synthesis or they are commercially available.

Frequently used yeasts promoters in the production of corresponding expression plasmids contain promoters which control the expression particularly efficiently in the yeast system, such as PGK promoter (Tuite, M. F. et al., The EMBO Journal 1, 603–608, 1982; Hitzeman, R. A. et al., Science 219,620–625, 1983), PH05 promoter (Hinnen, A., & Meyhack, B., Current Topics in Microbiology and Immunology 96,101–11.7, 1982; Kramer, R. A. et al., Proc. Natl. Acad. Sci. USA 81, 367–370, 1984), GAPDH promoter (Urdea, M. S. et al. Proc. Natl. Acad. Sci. USA 80, 7461–7465, 1983), GAL10 promoter (Broach et al., Experimental Manipulation of Gene Expression, 83–117, 1983), enolase (ENO) -promoter (Holland, M. J. et al., J. Biol. Chem. 256, 1385–1395, 1981), α-factor promoter (Bitter, G.-A. et al., Proc. Natl. Acad. Sci. USA 81, 5330–5334; Yakota, T. et al., Miami Winter Syrup. 17. Meet. Adv. Gene Technol.2, 49–52,1985) or ADHI promoter (Ammerer, G., Methods in Enzymology 101, 192–201, 1983; Hitzeman, R. A. et al., Nature 293, 717–722, 1981).

It is also possible to use promoters of other glycolytic enzymes (Kawasaki and Fraenkel, Biocbem. Biophys. Res. Comm. 108, 1107–1112, 1982), such as hexokinase, pyruvate decarboxylase, pbosphofructokinase, glucose-6-phosphate isomerase, phosphoglucose isomerase and glucokinase. When constructing suitable expression plasmids, the termination sequences associated with these genes may also be included in the expression vector at the 3' end of the sequence which is to be expressed, in order to provide polyadenylation and termination of the mRNA. Other promoters which also have the advantage of transcription controlled by growth conditions are the promoter regions of alcohol dehydrogenase-2, isocytochrome C, the degradation enzymes coupled to nitrogen metabolism, the above-mentioned glycerine aldehyde-3-phosphate dehydrogenase (GAPDH) and the enzymes which are responsible for metabolising maltose and galactose. Promoters which are regulated by the yeast mating type locus, for example promoters of the genes BAR1, MECI, STE2, STE3 and STE5, may be used in temperature-regulated systems by the use of temperature-dependent sir mutations (Rhine, Ph.D. Thesis, University of Oregon, Eugene, Oreg. (1979), Herskowitz and Oshima, The Molecular Biology of the Yeast Saccharomyces, Part I, 181–209 (1981), Cold Spring Harbour Laboratory)). These mutations affect the expression of the resting mating type cassettes of yeast and thus indirectly the mating type dependent promoters. Generally, however, any plasmid vector which contains a yeast-compatible promoter, origin of replication and termination sequences, is suitable.

If the expression of hMn-SOD is to take place in bacteria, it is preferable to use promoters which result in a high rate of synthesis of mRNA and which are also inducible. Known promoters which are used contain the beta-lactamase (penicillinase) and lactose promoter systems (Chang et al., Nature 275, 615 (1978); Itakura et al., Science 198, 1056 (1977); Goeddel et al., Nature 281, 544 (1979) including the UV5 promoter (Silverstone, A. E et al., Proc. Natl. Acad. Sci. USA 66, 773–779, 1970) and tryptophan (trp) promoter systems (Goeddel et al., Nucleic Acids Res. 8, 4057 (1980); European patent application, publication No. 0036 776). Moreover, other microbial promoters have also been developed and used. The gene sequence for hMn-SOD may be transcribed, for example, under the control of the lambda-$P_L$ promoter. This promoter is known as one of the particularly powerful, controllable promoters. Control is possible by means of a thermolabile repressor cI (e.g. cI857), to which adjacent restriction cutting sites are known. Furthermore, it is also possible to use the promoter of alkaline phosphatase from *E. coli* (Ohsuye, K. et al., Nucleic Acids Res. 11, 1283–1294, 1983) and hybrid promoters such as, for example, the tac-promoter (Amann, E. et al., Gene 25, 167–178, 1983; De Boer, H. A. et al., Proc. Natl. Acad. Sci. USA. 80 21–25, 1983). The use of promoters of this kind (lacuv5 lacZ SD, tac) which can be carried and vectors for preparing fused and non-fused eukaryotic proteins in *E. coli* is described in T. Maniatis et al., Molecular Cloning, Cold Spring Harbor Laboratory, 1982, especially page 412ff. The expression and translation of an hMn-SOD sequence in bacteria may also be carried out under the control of other regulatory systems which may be regarded as "homologous" to the organism in its untransformed state. For example, it is also possible to use promoter-operator systems such as arabinose operator, colicin E1 operator, galactose operator, alkaline phosphatase operator, trp operator, xylose A operator and the like or parts thereof.

For the cloning or expression of hMn-SOD in bacteria, for example in *E. coli*, or in yeasts, for example in *S. cerevisiae*, there are well known vectors available, of which, for the former host systems, it is advantageous to use the pBR plasmids (Bolivar, F. et al., Gene 2, 95–113, 1977), pUC plasmids (Vieira, I., Messing I., Gene 19, 259–268, 1982) pOP plasmids (Fuller, F., Gene 19, 43–54, 1982), pAT plasmids (Windass, J. D., et al., Nucleic Acids Res. 10, 6639–6657, 1982), pHV plasmids (Ehrlich, S. D., Proc. Natl. Acad. Sci. USA 75, 1433–1436, 1977), lambda vectors including phasmids (Brenner, S. et al., Gene 17, 27–44, 1982), cosmids (Collins, J., Hohn, B., Proc. Natl. Acad. Sci. USA 75, 4242–4246, 1979) and the other vectors known from the literature (e.g. Maniatis, T. et al., Molecular Cloning, Cold Spring Harbor Laboratory, 1982), particularly pBR and pUC derivatives, for example pBR322 and pUC18.

Suitable expression vectors in yeasts are integrating (YIp), replicating (YRp) and episomal (YEp) vectors (Struhl, K. et al., Proc. Natl. Acad. Sci. USA 76, 1035–1039, 1979; Stinchcomb, D. T. et al., Nature 282, 39–43, 1979; Hollenberg, C. P., Current Topics in Microbiology and Immunology 96,119–144, 1982), preferably YEp13 (Broach, J. R. et al., Gene 8,121–133, 1979), YIp5 (Struhl, K. et al., 1979 see above, ATCC 37061) and pJDB207 (DSM 3181) or pEAS102. The vector pEAS102 may be obtained by digesting YIp5 partially with PstI and totally with BamHI and ligating the isolated 4.3 kb fragment (which contains the URA3 gene) with the 4.4 kb BamHI/PstI fragment of pJDB207.

In addition to microorganisms, cultures of multicellular organisms are also suitable host organisms for the expression of hMn-SOD. In theory, any of these cultures may be used, whether obtained from vertebrate or invertebrate animal cultures. However, the greatest interest has been in vertebrate cells, with the result that the multiplication of vertebrate cells in culture (tissue culture) has become a routine method in recent years (Tissue Culture, Academic Press, Editors Kruse and Patterson, (1973)). Examples of useful host cell lines of this kind include VERO and HeLa cells, Golden Hamster Ovary (CHO) cells and W138, BHK, COS-7 and MDCK cell lines. Expression vectors for these cells generally contain a replication site, a promoter which is located in front of the hMn-SOD to be expressed, together with any necessary ribosome binding site, RNA splicing site, polyadenylation site and transcriptional termination sequences.

When used in mammalian cells, the control functions in the expression vector are often obtained from viral material. For example, the promoters normally used originate from papova viruses such as polyoma viruses, papilloma viruses, Simian Virus 40 (SV 40) and from retroviruses and adenovirus Type 2. The early and late promoters of SV 40 and their applications have frequently been described. Furthermore it is also possible and often desirable to use promoter or control sequences or splicing signals which are originally linked to the desired genetic sequences, provided that these control sequences are compatible with the host cell systems. Thus, SV40 vectors are known in which an exogenic eukaryotic DNA with its own promoter sequences and splicing signals, as well as the late SV40 promoter, will yield a stable transcript.

A replication starting point may either be provided by corresponding vector construction in order to incorporate an exogenic site, for example from SV 40 or other viral sources (e.g. polyoma, adeno, VSV, PBV, etc.) or it may be provided by the chromosomal replication mechanisms of the host cell. If the vector is integrated into the host cell chromosome, the latter measure is usually sufficient.

Transformation of the cells with the vehicles can be achieved by a number of processes. For example, it may be effected using calcium, either by washing the cells in magnesium and adding the DNA to the cells suspended in calcium or by subjecting the cells to a coprecipitate of DNA and calcium phosphate. During the subsequent gene expression, the cells are transferred to media which select for transformed cells.

In the intracellular production of hMn-SOD the enzyme may be isolated by centrifuging the cells off after a suitably high cell density has been reached and then enzymatically or mechanically opening them up. Purification of the hMn-SOD according to the invention may be carried out by known biochemical methods for purifying proteins or enzymes, such as dialysis, electrophoresis, precipitation, chromatography or combinations of these methods. If the enzyme is secreted from the cell, analogous methods of protein purification are carried out in order to obtain hMn-SOD from the culture medium in pure form.

The hMn-SOD according to the invention purified by these methods has a biological activity spectrum identical to the genuine enzyme both in vivo and in vitro.

These activities include both immunological properties (e.g. cross-reaction with antibodies of genuine hMn-SOD against the hMn-SOD according to the invention) and also biochemical and enzymatic activities. In order to characterise hMn-SOD biochemically and enzymatically, the method described by Marklund, S. (Marklund, S. & Marklund, G., Eur. J. Biochem. 47, 469–474, 1974) may be used, for example, according to which a strict distinction must be drawn between enzymes containing Cu/Zn and those containing Mn, for example by the addition of KCN (which inhibits Cu/Zn-SOD but not Mn-SOD) or using the different pH dependencies of their activities (see particularly Ysebaert-Vanneste, M., Vanneste, W. H., Anal. Biochem. 107, 86–95, 1980).

The polypeptide according to the invention includes not only the mature hMn-SOD which is described in detail but any modification of this enzyme. These modifications include, for example, shortening of the molecule at the N- or C-terminal end, and the substitution of amino acids by other groups, which do not substantially affect the enzyme activity.

The invention relates not only to genetic sequences which code specifically for the hMn-SOD which is described and demonstrated in the examples, but also to modifications which are easily and routinely obtainable by mutation, degradation, transposition or addition. Any sequences which code for the hMn-SOD according to the invention (i.e. which have the corresponding, known biological activity spectrum) and which are degenerate compared with those shown, are also included; experts in this field will be able to degenerate DNA sequences, particularly in the coding regions. Similarly, any sequence which codes for a polypeptide with the activity spectrum of the authentic hMn-SOD and which hybridises with the sequences shown (or parts thereof) under stringent conditions is also included.

The particular conditions which constitute stringent conditions under which hybridisation (including pre-washing, pre-hybridisation, hybridisation and washing) should be carried out are defined in the prior art. For hybridising oligonucleotides against a gene bank ("gene bank screening") the conditions described by Wood, I. M. et al. should preferably be used (Proc. Natl. Acad. Sci. USA 82, 1582–1588, 1985). To test whether a specific DNA sequence hybridises with one of the DNA sequences according to the invention which code for hMn-SOD—either via in situ hybridisation against plaques or colonies of bacteria or via Southern Blotting—the methods and conditions described in detail by Maniatis, T. et al. should be adopted (Maniatis T. et al., Molecular Cloning, Cold Spring Harbor Laboratory, 1982, particularly pages 326–328 and 387–389). All signals which are clearly distinguishable against the background therefore indicate a positive hybridisation signal.

More specifically, the problems described above are solved by preparing the RNA from human tissue, preferably from human placenta tissue. Whereas tissue culture cells can be disintegrated directly with hot phenol, tissue for this type of extraction first has to be broken up in deep-frozen condition, advantageously in the presence of powdered or granular dry ice or in liquid nitrogen (e.g. Starmix).

Aggregates of mRNA and other RNAs formed by phenol may be broken up again using formamide or by heating (e.g. to 65° C.). A preferred method of isolating RNA is the Chirgwin method (Chirgwin, J. M. et al., Biochemistry 18, 5294–5299, 1979). The poly(A)$^+$ RNA may be conveniently purified from the isolated protein and DNA preparation by affinity chromatography, e.g. poly(U) Sepharose or oligo(dT) cellulose, since eukaryotic mRNA populations generally have a poly(A) tail at their 3' end (Aviv, H., Leder, P., Proc.Natl.Acad. Sci. USA 69, 1409–1412, 1972; Lindberg, U., Persson, T., Eur. J. Biochem. 31, 246–254, 1972). Isolation of the poly(A)$^+$ RNA may preferably be carried out using the method described by Auffray (Auffray, C., Rougeon, F., Eur. J. Biochem. 107, 303–314, 1980).

The purified mRNA may be concentrated by dividing up the entire mRNA fraction according to size (e.g. by centrifuging in a sucrose gradient. The desired mRNA may be detected, for example, using known in vitro protein biosynthesis systems (reticulocytes, oocytes of *Xenopus laevis*).

The purified mRNA or the concentrated fraction is used as a template for synthesising the first strand of the cDNA, which is done using reverse transcriptase and a primer. The primers used may be either oligo (dT) or synthetic primers; the latter may be obtained using the known amino acid sequence of hMn-SOD and make it possible to carry out repeated priming of reverse transcription (Uhlen, M. et al., EMBO Journal 1, 249–254, 1982).

In the present invention the synthesis of the first strand of the cDNA was started with oligo(dT) 12–18 as primer in the presence of dNTPs.

The second strand of the cDNA may be synthesised by various known methods, of which priming with a complementary primer (Rougeon, F., Mach, B., J.Biol. Chem. 252, 2209–2217, 1977), self-priming with the aid of a "hairpin" structure located at the 3' end of the cDNA (Efstratiadis, A. et al., Cell 7, 279, 1976) or with an Okazaki fragment-like primer formed by RNaseH (Gubler, U., Hoffmann, B. J., Gene 25, 263, 1982) may be mentioned in particular. The preferred method according to the present invention is the one described by Huynh, T. V. (Huynh, T. V. et al., in DNA Cloning Vol I, (D. M. Glover ed.), chapter 2, pages 49–78, 1985). The double-stranded cDNA obtained by this method can be cloned or packaged directly in a suitable vector, e.g. in a cosmid, insertion or substitution vector, more particularly in a lambda vector, preferably in λgt10 (Huynh, T. V. et al., 1985). There are a number of known methods of cloning in lambda, of which "homopolymer tailing" using dA-dT or dC-dG or the linker method with synthetic linkers should be mentioned by way of example (Maniatis, T. et al., Molecular Cloning, Cold Spring Harbor Laboratory, 1982; Huynh, T. V. et al., DNA Cloning Vol. I (D. M., Glover ed.) 1985, 1980; Watson, C. J., Jackson, F. dto, 1985, chapter 3). In the cloning of the cDNA according to the invention, this is inserted into the EcoRI site of λgt10. The in vitro packaging and cloning of the cDNA according to the invention and the construction of the cDNA gene bank were carried out according to Huynh, T. V. et al. 1985, pages 49–78.

Using the phage population obtained, which represents a cDNA gene bank from placental tissue, amplification and plaque purification were carried out by infecting a suitable host, particularly E. coli, preferably E. coli C 600, and, respectively, by securing the lytic replication cycle of lambda.

The cDNA gene bank was investigated under stringent hybridisation conditions with radioactively labelled synthetic oligonucleotides which had been obtained using the published amino acid sequence (Barra, D. et al., Oxy Radicals and their scavenger Systems, Vol. 1, 336–339, 1983). In the present invention, the method of hybridisation in situ described by Benton and Davis (Benton, W. D., Davis, R. W., Science 196, 180–182, 1977) was used. Preferably, two mixtures, each consisting of eight synthetic 23-mer oligonucleotides of formulae Va and Vb were used, which are colinear with amino acids 39 to 46 and 200–207, respectively, of the amino acid sequence published by Barra, D. et al. (see above) and which take into account the degeneracy of the genetic code. The last base at the 5' end of these DNA probes lacks the wobble base for the entire codon for Gln (amino acid 46) or Glu (amino acid 207). A, G, C and T represent the corresponding nucleotides whilst I represents inosine.

|   |   |   | Formula Va |   |   |   |
|---|---|---|---|---|---|---|
| TGITA | C T | TT | C T | TC | C T | TCIGTIACITT |

|   |   |   | Formula Vb |   |   |   |
|---|---|---|---|---|---|---|
| TCIGTIAC |   | TT | C T | TCCCA | A G | TTIAT |
|   |   |   | A G |   |   |   |

The oligonucleotide probes may be prepared by known chemical methods of synthesis. For the present invention, a Model 381A DNA Synthesizer (Applied Biosystems) was used.

The synthesis of all possible combinations of these two DNA probes ensures that at least one of the oligonucleotides present forms an optimum pair with the single-stranded DNA region of the desired hMn-SOD gene, complementary to the probe. The use of two independent pools of 23-met oligonucleotides reduces the possibility of selecting "false" positives.

After isolation of inherently homogeneous plaques which have been identified by positive signals after hybridisation with the two 23-mer DNA probes, it was possible to isolate seven recombinant phages and to sequence 500 to 1000 bp long EcoRI fragments of their DNA. After sequence analysis of these EcoRI fragments by the Sanger method (Sanger et al., Proc. Natl. Acad. Sci. USA 74, 5463–5467, 1977; Sanger F et al., FEES Letters 87, 107–111, 1978) and after subcloning into the EcoRI site of the M13 vector (Bluescribe, Vector Cloning Systems) and transformation in E. coli, for example E. coli JM101, it was discovered that the EcoRI fragments contain cDNA inserts which code for hMn-SOD from amino acid 22 (clones BS5, BS8, BS9, BS13, BSXIII) or from amino acid 26 (clones BS3, BS12).

However, it was also found, surprisingly, that some deviations from the amino acid sequence described by Barra, D. et al. (1984, loc.cit.) also arose from the DNA sequences obtained:

| Clone | Amino acid | Codon | Amino acids derived | Amino acid according to Barra, D. et al., 1984 |
|---|---|---|---|---|
| BS3, BS12, | 29 | CAG | Gln | Lys (29) |
| BS5, BS9, BS13 BSXIII | 29 | AAG | Lys | Lys (29) |
| BS3, BS12, BS13, BS5, BS9 | 42 | GAG | Glu | Gln (42) |
| BSXIII | 88 | GAG | Glu | Gln (88) |
|  | 29 | AAG | Lys | Lys (29) |
| BS8 | 42 | GAG | Glu | Gln (42) |
|  | 88 | GAG | Glu | Gln (88) |
|  | 109 | GAG | Glu | Gln (109) |
|  | 124 | GGT | Gly | Δ |
|  | 125 | TGG | Trp | Δ |
|  | 139 | GAA | Glu | Gln (129) |

The DNA sequence of a 617 bp long EcoRI fragment which could be isolated from one of the clones obtained, e.g. BS8, is shown in FIG. 1. The EcoRI fragment contains a 532 bp long sequence coding for hMn-SOD and a 51 bp long non-translated region, including a poly(A)$_{30}$ tail. Sections of linker sequences are also shown, up to the (complete) EcoRI sites.

Positions 30 to 33 show a ThaI cutting site whilst at positions 367 to 372 there is a BamHI site. Surprisingly, there are codons at positions 53 to 61, 155 to 163, 176 to 184 and 500 to 508, which are colinear for potential N-glycosylation sites of the corresponding amino acids according to the general amino acid arrangements Asn-X-Thr and Asn-X-Set characteristic thereof, wherein X represents valine, histidine or leucine, for example, whereas the Cu/Zn-SOD of the cytosol has only one such amino acid combination.

The amino acid differences from the amino acid sequence of Barra, D. et al. (Barra, D. et al., J. Biol. Chem. 259, 12595–12601, 1984), which were derived from the EcoRI fragment obtained, have already been discussed hereinbefore.

Various strategies may be adopted in order to obtain the missing bases at the 3' and/or 5' termini of the hMn-SOD DNA partial sequence from the cDNA gene bank to prepare a complete hMn-SOD gene. For example, the cDNA obtained may be used as a hybridisation probe against a genomic gene bank, in order to obtain the sequence coding for the entire enzyme, or the method described by H. Kakidani may be used, for example, using synthetic oligonucleotides complementary to the mRNA as specific primers for the reverse transcription (Kakidani, H. et al., Nature 298, 245–249, 1982). However, it is also possible to synthesise the missing end of the cDNA sequence chemically by means of the known amino acid sequence (Barra, D. et al., J. Biol. Chem. 259, 12595–12601, 1984) and to link it to the cDNA found, thereby obtaining a defined end.

In the latter method, in order to prepare the complete DNA sequence according to the invention for hMn-SOD, the 5' end was completed by two oligonucleotides of formulae VIa and VIb which advantageously had XhoI/XbaI - or XbaI/NcoI - projecting ends. According to the invention, the 3' end of the ADHI promoter was taken into consideration at the 5' end of the coding strand (Formula VIa)

Sequencing of the clones BS5, BS9, BS13, BSXIII and clones BS3 and BS12 showed that the sequences of clones BS5, BS9, BS13 and BSXIII are identical with clone BS8. As already stated, clones BS3 and BS12 differ from clone BS8 in amino acid 29 (CAG instead of AAG or Gln instead

Formula VIa

| 5 |   | TCGAG | TATACA | ATG | AAG | CAC | TCT | TTG | CCA | GAC | TTG |
|---|---|-------|--------|-----|-----|-----|-----|-----|-----|-----|-----|
| 3 |   |       | C ATATGT | TAC | TTC | GTG | AGA | AAC | GGT | CTG | AAG |
|   | XhoI |    |        |     |     |     |     |     |     |     |     |
|   |   | CCA   | TAC    | GAC | TAC | GGT | GCT |     |     |     |     |
|   |   | GGT   | ATG    | CTG | ATG | CCA | CGA | GATC |    |     |     |
|   |   |       |        |     |     |     |     | XbaI |    |     |     |

Formula VIb

| 5 |   | CTAGAA | CCA | CAC | ATC | AAT | GCT | CAA | ATC | ATG | CAA |
|---|---|--------|-----|-----|-----|-----|-----|-----|-----|-----|-----|
| 3 |   | TT     | GGT | GTG | TAG | TTG | CGA | GTT | TAG | TAC | GTT |
|   | XbaI |     |     |     |     |     |     |     |     |     |     |
|   |   | TTG    | CAC | CAC | TCT | AAG | CAC |     |     |     |     |
|   |   | AAC    | GTG | GTG | AGA | TTC | GTG | GTAC |   |     |     |
|   |   |        |     |     |     |     |     | NcoI |   |     |     |

After combination of the two synthetic oligonucleotides of formulae VIa and VIb, cloning into a suitable vector, for example a correspondingly modified pUC18 derivative and addition of the ThaI/EcoRI fragment of the cDNA according to the invention from one of the clones obtained, the 5' end of which has at least the ThaI site, it is possible to obtain a plasmid which contains a complete cDNA of the hMn-SOD gene in the correct reading frame corresponding to formulae VIIa and VIIb, without the ThaI sites.

of Lys, formula Ib, IIIb and IVb). Otherwise, there is 100% homology with clone BS8 up to base 573 of the EcoRI fragment shown in FIG. 1 (... TA*A ACC ACG ATC GTT ATG CTG$^{573}$). Apart from this base, the two clones BS3 and BS12 are identical with respect to the 5-ut (untranslated) region shown in Formula VIII.

Formula VIIa

| 5' ATG | AAG | CAC | TCT | TTG | CCA | GAC | TTG | CCA | TAC | GAC | TAC | GGT |
|--------|-----|-----|-----|-----|-----|-----|-----|-----|-----|-----|-----|-----|
| GCT    | CTA | GAA | CCA | CAC | ATC | AAT | GCT | CAA | ATC | ATG | CAA | TTG |
| CAC    | CAC | TCT | AAG | CAC | CAT | GCG | GCC | TAC | GTG | AAC | AAC | CTG |
| AAC    | GTC | ACC | GAG | GAG | AAG | TAC | CAG | GAG | GCG | TTG | GCC | AAG |
| GGA    | GAT | GTT | ACA | GCC | CAG | ATA | GCT | CTT | CAG | CCT | CCA | CTG |
| AAG    | TTC | AAT | GGT | GGT | GGT | CAT | ATC | AAT | CAT | AGC | ATT | TTC |
| TGG    | ACA | AAC | CTC | AGC | CCT | AAC | GGT | GGT | GGA | GAA | CCC | AAA |
| GGG    | GAG | TTG | CTG | GAA | GCC | ATC | AAA | CGT | GAC | TTT | GGT | TCC |
| TTT    | GAC | AAG | TTT | AAG | GAG | AAG | CTG | ACC | GCT | GCA | TCT | GTT |
| GGT    | GTC | CAA | GGC | TCA | GGT | TGG | GGT | TGG | CTT | GGT | TTC | AAT |
| AAG    | GAA | CGG | GGA | CAC | TTA | CAA | ATT | GCT | GCT | TGT | CCA | AAT |
| CAG    | GAT | CCA | CTG | CAA | GGA | ACA | ACA | GGC | CTT | ATT | CCA | CTG |
| CTG    | GGG | ATT | GAT | GTG | TGG | GAG | CAC | GCT | TAC | TAC | CTT | CAG |
| TAT    | AAA | AAT | GTC | AGG | CCT | GAT | TAT | CTA | AAA | GCT | ATT | TGG |
| AAT    | GTA | ATC | AAC | TGG | GAG | AAT | GTA | ACT | GAA | AGA | TAC | ATG |
| GCT    | TGC | AAA | AAG | TAA |     |     |     |     |     |     |     |     |

Formula VIIb

| 5' ATG | AAG | CAC | TCT | TTG | CCA | GAC | TTG | CCA | TAC | GAC | TAC | CGT |
|--------|-----|-----|-----|-----|-----|-----|-----|-----|-----|-----|-----|-----|
| GCT    | CTA | GAA | CCA | CAC | ATC | AAT | GCT | CAA | ATC | ATG | CAA | TTG |
| CAC    | CAC | TCT | CAG | CAC | CAT | GCG | GCC | TAC | GTG | AAC | AAC | CTG |
| AAC    | GTC | ACC | GAG | GAG | AAG | TAC | CAG | GAG | GCG | TTG | GCC | AAG |
| GGA    | GAT | GTT | ACA | GCC | CAG | ATA | GCT | CTT | CAG | CCT | GCA | CTG |
| AAG    | TTC | AAT | GGT | GGT | CAT | ATC | AAT | CAT | AGC | ATT | TTC |     |
| TGG    | ACA | AAC | CTC | AGC | CCT | AAC | GGT | GGT | GGA | GAA | CCC | AAA |
| GGG    | GAG | TTG | CTG | GTA | GCC | ATC | AAA | CGT | GAC | TTT | GGT | TCC |
| TTT    | GAC | AAG | TTT | AAG | GAG | AAG | CTG | ACG | GCT | GCA | TCT | GTT |
| GGT    | GTC | CAA | GGC | TCA | GGT | TGG | GGT | TGG | CTT | GGT | TTC | AAT |
| AAG    | GAA | CGG | GGA | CAC | TTA | CAA | ATT | GCT | GCT | TGT | CCA | AAT |
| CAG    | GAT | CCA | CTG | CAA | GGA | ACA | ACA | GGC | CTT | ATT | CCA | CTG |
| CTG    | GGG | ATT | GAT | GTG | TGG | GAG | CAC | GCT | TAC | TAC | CTT | CAG |
| TAT    | AAA | AAT | GTC | AGG | CCT | GAT | TAT | CTA | AAA | GCT | ATT | TGG |
| AAT    | GTA | ATC | AAC | TGG | GAG | AAT | GTA | ACT | GAA | AGA | TAC | ATG |
| GCT    | TGC | AAA | AAG | TAA |     |     |     |     |     |     |     |     |

Formula VIII

```
5'AAG CAC TCT ... [Formula IIIb] ... AAA AAG TAA ACC ACG
ATC    GTT    ATG    CTG    AGTAT  GTTAA  GCTCT  TTATG  ACTGT  TTTTG  TAGTG
GTATA  GAGTA  CTGCA  GAATA  CAGTA  AGCTG  CTCTA  TTGTA  GCATT  TCTTG
ATGTT  GCTTA  GTCAC  TTATT  TCATA  AACAA  CTTTA  TGTTC  TGAAT  AATTT
CTTAC  TAAAC  ATTTT  GTTAT  TGGGC  AAGTG  ATTGA  AAATA  GTAAA  TGCTT
AGTGT  GATTG  AATCT  GATTG  GACAT  TTTCT  TCAGA  GAGCT  AAATT  ACAAT
TGTCA  TTTAT  AAAAC  CATCA  AAAAT  ATTCC  ATCCA  TATAC  TTTGG  GGACT
TGTAG  GGATG  CCTTT  CTAGT  CCTAT  TCTAT  TGCAG  TTATA  GAAAA  GTAGT
CGACCATGCGGAATTC
Linker         EcoRI
```

Furthermore, a number of cDNA clones were isolated from a cDNA gene bank (placenta) using λgt11. This cDNA gene bank was prepared in the same way as the cDNA gene bank described in the Examples from placenta DNA in λgt10. One of the clones isolated from λgt11, namely clone 4, was subcloned in Bluescribe M13+ in the manner described. Sequencing was carried out by repeated priming with the synthetic 17mer oligonucleotides EBI 760:5' AGATACATGGCTTGCAA 3'
EBI 765:5' CTCTGAAGAAAATGTCC 3'
EBI 782:5' GGAGATGTTACAGCCCA 3'
EBI 785:5' AAGGAACGGGGACACTT 3'

Clone 4 is identical to clones BS3 and BS12 from λgt10 apart from amino acid 29 (AAG or Lys) and a ... TCTA ... sequence at the 3' end adjoining the multicloning site. Although the analysed DNA sequence of the remaining 61 bases of the 5' end (before formula Ia, clone BS8, corresponding to codons +1 to +21 corresponding to Lys to Glu) shows some base changes compared with the derived DNA sequence (Formula II, contained in Formula IIIb), the translation of this DNA section does not produce any differences from Barra et al., 1984. A leader sequence in front of the ATG was also analysed. Formula IX shows the sequence of clone 4 found.

in pES103 with the ADHI promoter (DSM 4013). pES103 is obtained by incorporating the 1500 bp long BamHI/XhoI fragment of the ADHI promoter (e.g. Ammerer, G., Methods in Enzymology 101, 192–201, 1983) in the pUC18 derivative pES102, which contains an Xho linker in the HincII cutting site.

Instead of this ADHI promoter sequence originally of 1500 bp, it is also possible to use an ADHI promoter shortened to a length of about 400 bp as the BamHI/XhoI fragment. The shortened ADHI promoter (ADHIk) is obtained by digesting plasmid pWS323E (DSM 4016) with BamHI/XhoI and isolating the ADHIk promoter.

For the correct termination, a suitable terminator sequence, conveniently an ADH terminator, preferably the ADHII terminator is ligated behind the hMn-SOD. The ADHII terminator (Beier, D. R., Young E. T., Nature 300, 724–728, 1982) can be obtained by SphI digestion of pMW5-ADHII (Washington Research Foundation) as a fragment 1530 bp long and, after subsequent HincII digestion, as a final ADHII terminator (329 bp), or from plasmid pGD2 (DSM 4014) as a HindIII/XbaI fragment 336 bp long.

For expression in yeast, there are various yeast vectors available into which the expression cassettes with the hMn-SOD gene according to the invention can be incorporated, preferably YEp13 (Broach, J. R. et al., Gene 8, 121–133, Formula IX

```
                                                              EcoRI
                                                        (GGGCGAATTCCAGC)
-24                    -20                      -15
M     L     S     R     A     V     C     G     T     S     R     Q     L     P
ATG   TTG   AGC   CGG   GCA   GTG   TGC   GGC   ACC   AGC   AGG   CAG   CTG   CCT
-10                     -5                      -1    +1
P     V     L     C     Y     L     G     S     R     Q     K     H     S     L
CCG   GTT   TTG   GGG   TAT   CTG   GGC   TCC   AGG   CAG   AAG   CAC   AGC   CTC
+5                           +10                      +15
P     D     L     P     Y     D     Y     G     A     L     E     P     H     I
CCC   GAC   CTG   CCC   TAC   GAC   TAC   GGC   GCC   CTG   GAA   CCT   CAC   ATC
      +20   +21
N     A     Q     I
AAC   GCG   CAG   ATC ... [Formula Ia] ... AAA AAG TAA ACC
ACG    ATC    GTT    ATG    CTG    AGTAT  GTTAA  GCTCT  TTATG  ACTGT  TTTTG
TAGTG  GTATA  GAGTA  CTGCA  GAATA  CAGTA  AGCTC  TTATG  CTCTA  TTGTA
GCATT  TCTTG  ATGTT  GCTTA  GTCAC  TTATT  TCATA  AACAA  CTTAA
TGTTC  TGAAT  AATTT  CTTAC  TAAAC  ATTTT  GTTAT  TGGGC  AAGTG
ATTGA  AAATA  GTAAA  TGCTT  TGTGT  GATTG  AATCT  GATTG  GACAT
TTTCT  TCAGA  GAGCT  AAATT  ACAAT  TGTCA  TTTAT  AAAAC  CATCA
AAAAT  ATTCC  ATCCA  TATAC  TTTGG  GGACT  TGTAG  GGATG  CCTTT
CTAGT  CCTAT  TCTAT  TGCAG  TTATA  GAAAA  TCTA   GGAATTCGCCC
                                                 EcoRI-Linker
```

*Other sequenced clones show alanine (GCT) at position −9.

Other clones have 5'ut regions of different lengths.

The DNA sequences according to the invention may be incorporated in various expression vectors and expressed with the aid of the control elements described, for example 1979; ATCC 37115), pJDB 207 (DSM 3181, filed on 28.12.1984), YIp5 (Struhl, K. et al., Proc. Natl.Acad. Sci USA 76, 1035–1039, 1979; ATCC 37061), pEAS102 (pEAS102 can be obtained by digesting YIp5 partially with PstI and completely with BamHI and ligating the isolated 4.3 kb fragment which contains the URA3 gene with the 4.4 kb BamHI/PstI fragment of pJDB207).

With these yeast vectors which carry an expression cassette with the hMn-SOD gene according to the invention it is possible to transform suitable yeast cells by known methods. Suitable yeast cells for expression are preferably all those which are deficient for their own yeast-specific Mn-SOD and which contain a selectable yeast gene, such as HIS3, URA3, LEU2 and SUP, to name but a few. Mutants of this kind which contain, for example, mutated genes constructed in vitro or in vivo and contain them via a "transplacement" may be obtained by integrative transformation (e.g. Winston, F. et al., Methods in Enzymology 101, 211–228, 1983). The Mn-SOD gene of the yeast which is to be mutated is contained, for example, in plasmid pL41 as a BamHI fragment (van Loon et al., Gene 2.6, 261–272, 1983). Since the entire sequence of this BamHI fragment is known (Marres, C.A.M. et al., Eur.J.Biochem. 147, 153–161, 1985), the Mn-SOD gene of the yeast is obtainable even without pL41.

The hMn-SOD produced by such transformants can be obtained by known methods of protein isolation and protein purification. The cell decomposition may be carried out, for example, according to van Loon et al. (Proc. Natl. Acad. Sci. USA 83, 3820–3824, 1986).

For the expression of hMn-SOD in bacteria, preferably *E. coli*, more specifically *E. coli* HB101, C600 and JM101, it is possible to use the established expression systems mentioned hereinbefore. For this purpose, the DNA sequences according to the invention must be brought under the control of a powerful *E. coli* promoter (loc.cit.), not under a eukaryotic promoter. Examples of these known promoters are lac, lacuv5, trp, tac, trp-lacuv5, $\lambda P_L$, ompF and bla. The obligatory use of a ribosomal binding site to ensure efficient translation in *E. coli* has already been described in detail earlier.

In order to demonstrate the expression of the hMn-SOD activity by *E. coli*, the bacteria are disintegrated in a suitable conventional culture medium after incubation and the supernatant is tested for hMn-SOD activity as described (e.g. Marklund, S., Marklund, G., 1974; Ch. Beauchamp and I. Fridovich, Anal. Biochem. 44, 276–287, 1971; H. P. Misra and I. Fridovich, Arch.Biochem.Biophys. 2.8.3,511–515, 1977; B. J. Davis, Annals of the NY Academy of Sciences 121, 404–427, 1964; M. Ysebaert-Vanneste and W. H. Vanneste, Anal.Biochem. 107, 86–95, 1980).

The expression of the hMn-SOD gene may also be detected by labelling the proteins in maxicells. Plasmid-coded proteins may be labelled selectively in vivo using the maxicell technique (Sancar, A. et al., J. Bacteriol, 137, 692–693, 1979). The *E. coli* strain CSR603 (CGSC 5830) has no DNA repair mechanisms. A suitable dose of UV radiation destroys the bacterial chromosome, but some of the substantially smaller plasmid DNAs which are present in several copies per cell remain functional. After all the undamaged, replicating cells have been killed off by means of the antibiotic D-cycloserine and the endogenous mRNA has been consumed, only plasmid-coded genes are transcribed and translated in the remaining cells. The proteins formed may be radioactively labelled and detected by the incorporation of $^{35}$S-methionine. *E. coli* CSR603 is transformed with the expression plasmids by conventional methods and selected for transformed bacteria on ampicillin-containing agar plates. The preparation of the maxicells and the labelling of the proteins are carried out by the method of A. Sancar (1979, loc. cit.) A $^{14}$C-methylated protein mixture (Amersham) is used as the molecular weight standard. The plasmid containing only the promoter without the hMn-SOD gene is used as control.

After transformation of the host, expression of the gene and fermentation or cell cultivation under conditions in which the proteins according to the invention are expressed, the product can usually be extracted by known chromatographic methods of operation, so as to obtain a material which contains proteins with or without leader and tailing sequences. The hMn-SOD according to the invention can be expressed with a leader sequence at the N-terminus, which may be removed from some host cells as already described. If not, the leader polypeptide (if present) must be cleaved, as described hereinbefore, to obtain mature hMn-SOD. Alternatively, the sequence can be modified so that the mature enzyme is produced directly in the microorganism. The precursor sequence of the yeast mating pheromone MF-alpha-1 may be used for this case, to ensure correct "maturation" of the fused protein and the secretion of the products into the growth medium or the periplasmic space. The "secretion" of the hMn-SOD in yeast mitochondria may be effected by placing the leader sequence for the yeast Mn-SOD gene directly before the hMN-SOD gene.

Suitable leader sequences, for example those described by Marres C.A.M. et al., Eur. J. Biochem. 147, 153–161 (1985) or derivatives thereof, may either be of natural origin or may be isolated from corresponding eukaryotic cells (for example *S. cerevisiae*) or they may be produced synthetically. For example, a yeast-specific DNA presequence which is necessary for importing the hMn-SOD into the yeast mitochondrium may be obtained by ligating individual synthetic oligonucleotides. According to the invention, the complete presequence may be inserted between the start codon ATG and the first codon for the first amino acid of the mature hMn-SOD (Lys, e.g. AAG) or any desired portion of an N-terminal end thereof, for example in formulae II, IIIa, IIIb, VIa, VIIa, VIIb, VIII or XI. Similarly, a presequence of this kind may be incorporated directly after the ATG start codon and directly before the first codon of a DNA which is mutated from the genuine DNA sequence of hMn-SOD by sequence modifications and which codes for a protein with hMn-SOD activity.

A leader sequence which can be used according to the invention for the purpose of importing an hMn-SOD into the yeast mitochondrium is shown in formula X which follows, in which the known sequence GCA GCT (Marres, C.A.M. et al., 1985, loc. cit.) is substituted for GCT GCA (both triplets code for alanine) and a PvuII recognition site is created.

Formula X

PvuII
TTCGCGAAAACAGCTGCAGCTAATTTAACCAAGAAGGGTGGTTTGTCATTGCTCT
CCACCACAGCAAGGAGAACC

Preferably, the leader sequence, for example as in formula X, may be contained in the XhoI/XbaI fragment of formula VIa. This ensures that this 128 bp linker with the leader can be linked to the remaining hMn-SOD gene via the XhoI and XbaI sites in such a way that the leader sequence is located immediately after the start ATG and immediately before the first amino acid (lysine) of the hMn-SOD Formula XI XhoI                                                    PvuII Start
5'TCGAGTATACAATGTTCGCGAAAACAGCTGCAGCTAA
   CATATGTTACAAGCGCTTTTGTCGACGTCGATT
TTTAACCAAGAAGGGTGGTTTGTCATTGCTC
AAATTGGTTCTTCCCACCAAACAGTAACGAG
                                    Lysine
TCCACCACAGCAAGGAGAACCAAGCACTCTTT
AGGTGGTGTCGTTCCTCTTGGTTCGTGAGAAA
GCCAGACTTGCCATACGACTACGGTGCT3'
CGGTCTGAACGGTATGCTGATGCCACGAGATC
                                    XbaI Purification of the hMn-SOD from cells may be carried out by known methods.

The hMn-SOD according to the invention prepared by genetic engineering are suitable, owing to their biological/enzymatic spectrum of activity on the one hand and on account of the quantity of highly purified enzyme now available which has maximum possible immunological identity with genuine hMn-SOD, on the other hand, for every type of prevention, treatment and/or diagnosis in inflammatory, degenerative, neoplastic or rheumatic diseases, for wound healing, in autoimmune diseases and in transplants, and for the prevention and treatment of diseases which are accompanied by a deficiency of hMn-SOD or are causally linked thereto. For example, the clinical applications include those which may be inferred from Bannister W. H. and Bannister J. V. (Biological and Clinical Aspects of Superoxide and Superoxide Dismutase, Vol. 11B, Elsevier/North-Holland, 1980) and Michelson, A. M., McCord, J. M., Fridovich (Superoxide and Superoxide Dismutases, Academic Press, 1977). Furthermore, the following clinical applications should be considered: for perfusion wounds, strokes, alcohol-damaged livers, premature babies, possibly pancreatitis, acute respiratory diseases, (ARDs), emphysema, dialysis-damaged kidneys, osteoarthritis, rheumatoid arthritis, radiation-induced damage, sickle-cell anemia.

The hMn-SODs according to the invention are also suitable for increasing the shelf-life of solid or liquid foods.

The hMn-SODs according to the invention may be administered either systemically or topically, whilst in the former case conventional parenteral routes of administration (e.g. i.v., i.m., s.c., i.a.) and for the latter case the known preparations may be used (e.g. pastes, ointments, gels, tablets for sucking or chewing, powders and other galenic formulations which permit local resorption of the hMn-SOD preparations and pharmaceutically acceptable carriers). A therapeutically effective dosage range of around 4 mg, for example, per day may be used depending on individual criteria (e.g. the patients, the severity of the illness, etc).

LEGEND TO THE FIGURES

FIG. 1: EcoRI fragment from clone BS8 with the 532 bp long coding region from amino acid 22 of mature hMn-SOD, the 51 bp 3' ut region and the sequence portions of the linker. The potential N-glycosylation sites (overlined), the single ThaI and BamHI sites (underlined) are shown.

FIG. 2: Schematic strategy for construction of plasmid HSOD4 which contains the synthetic 5' end of the hMn-SOD gene as an XhoI/NcoI fragment.

Figure 3:
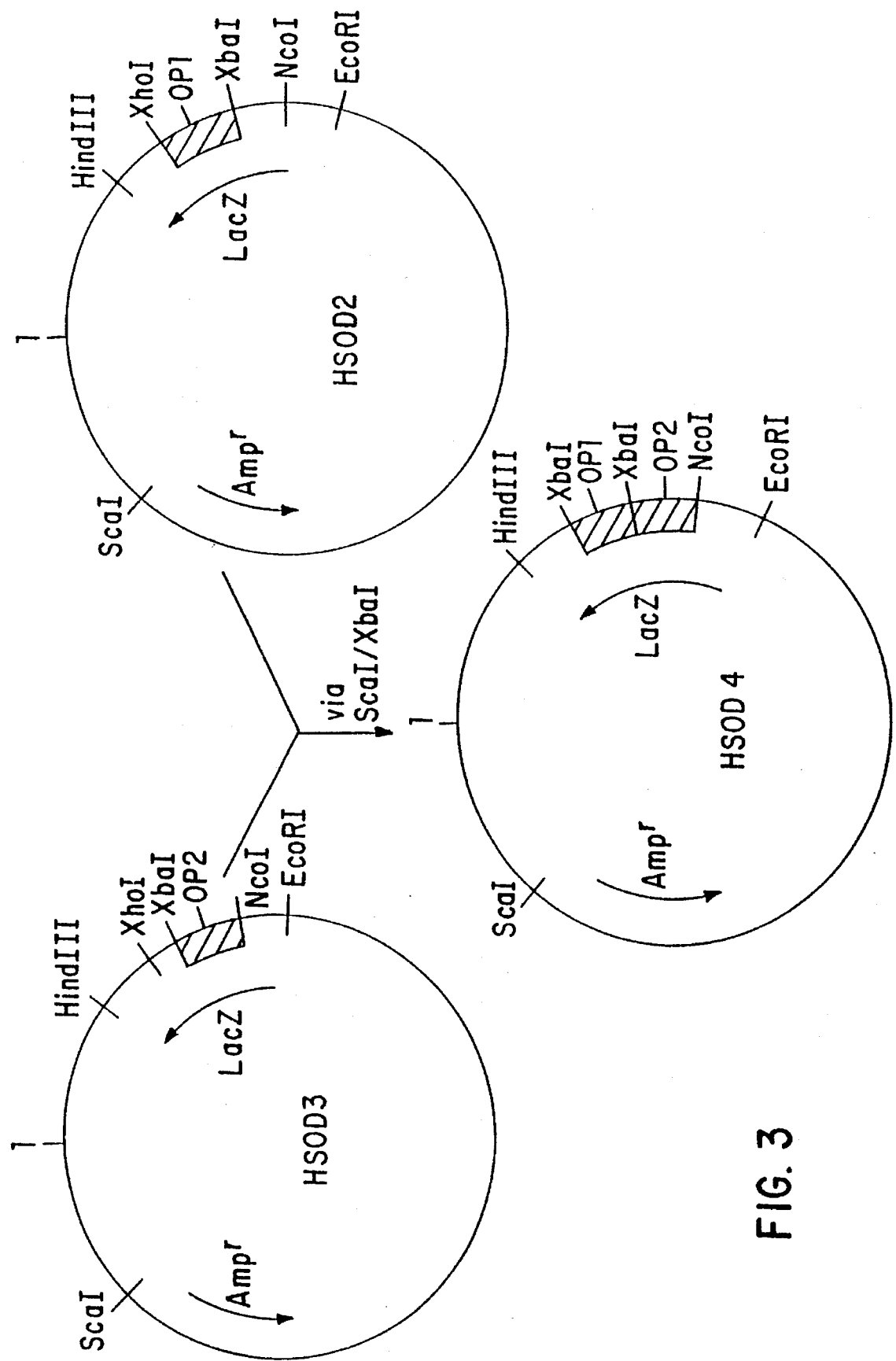

FIG. 3: Restriction maps of plasmids HSOD2 and HSOD3 and plasmid HSOD4 constructed therefrom.

Figure 4:
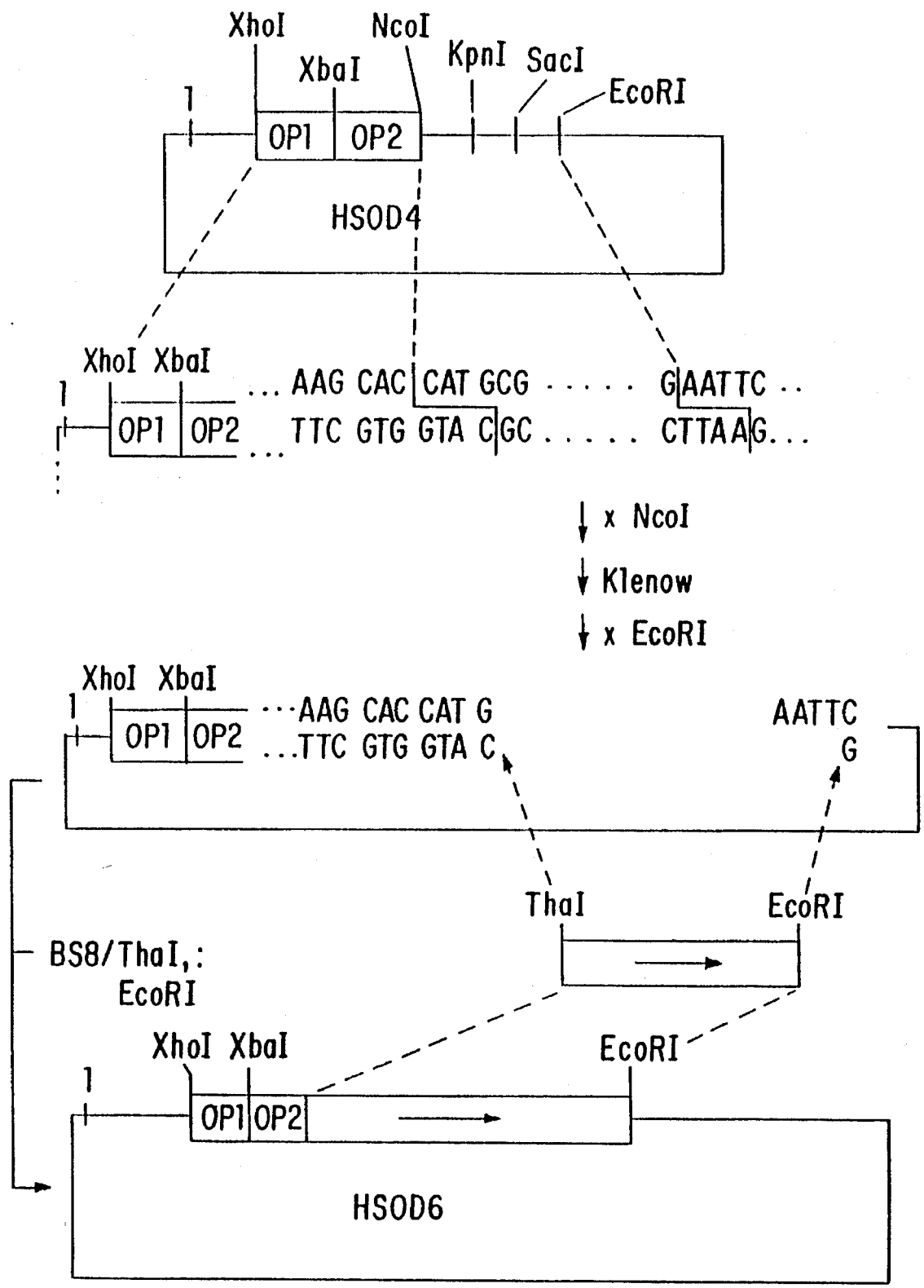

FIG. 4: Construction of a plasmid (HSOD6) with the complete cDNA for hMn-SOD, as an XhoI/EcoRI fragment.

Figure 5:
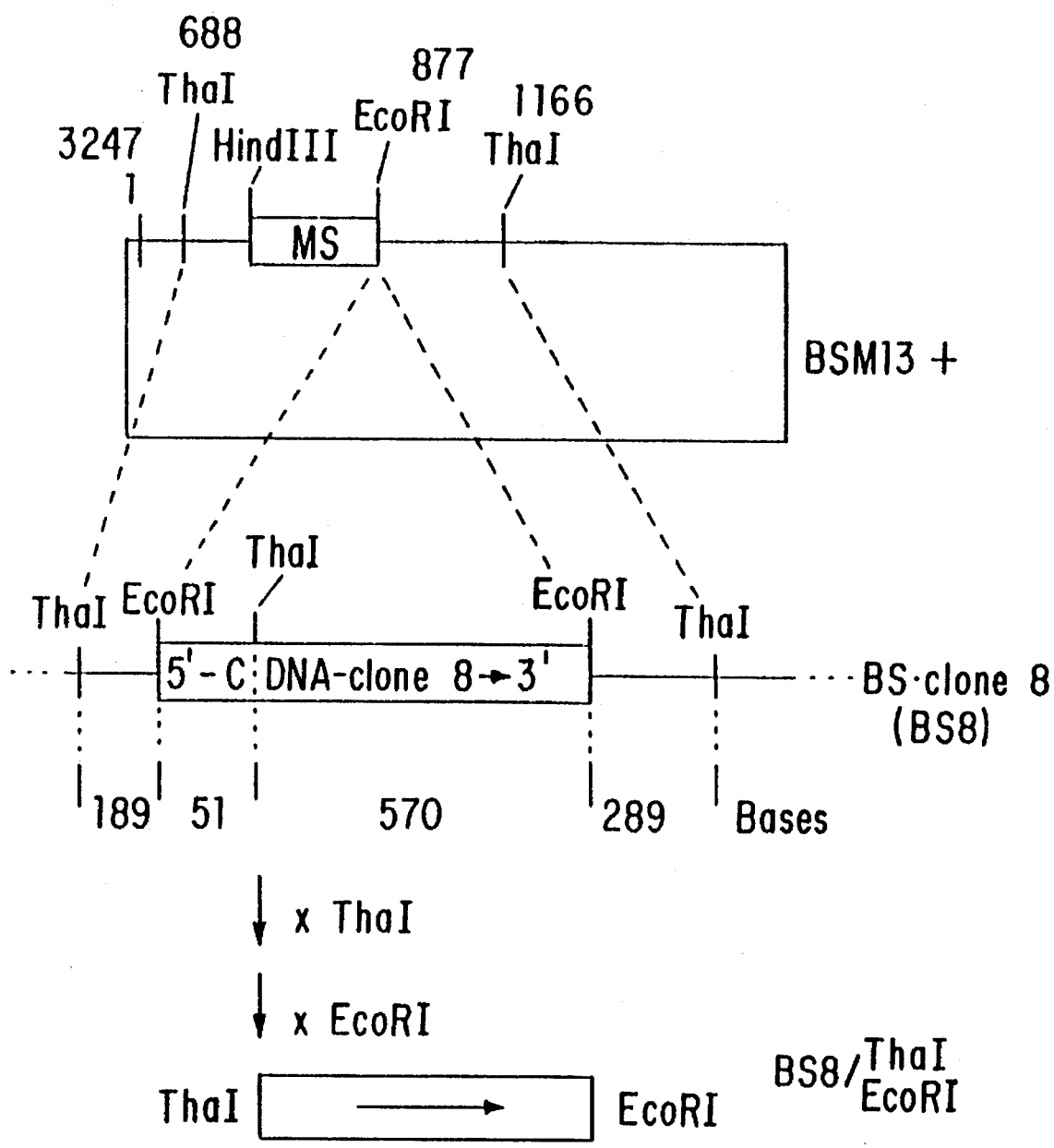

FIG. 5: Preparation of the ThaI/EcoRI fragment of hMn-SOD cDNA from clone BS8.

Figure 6:
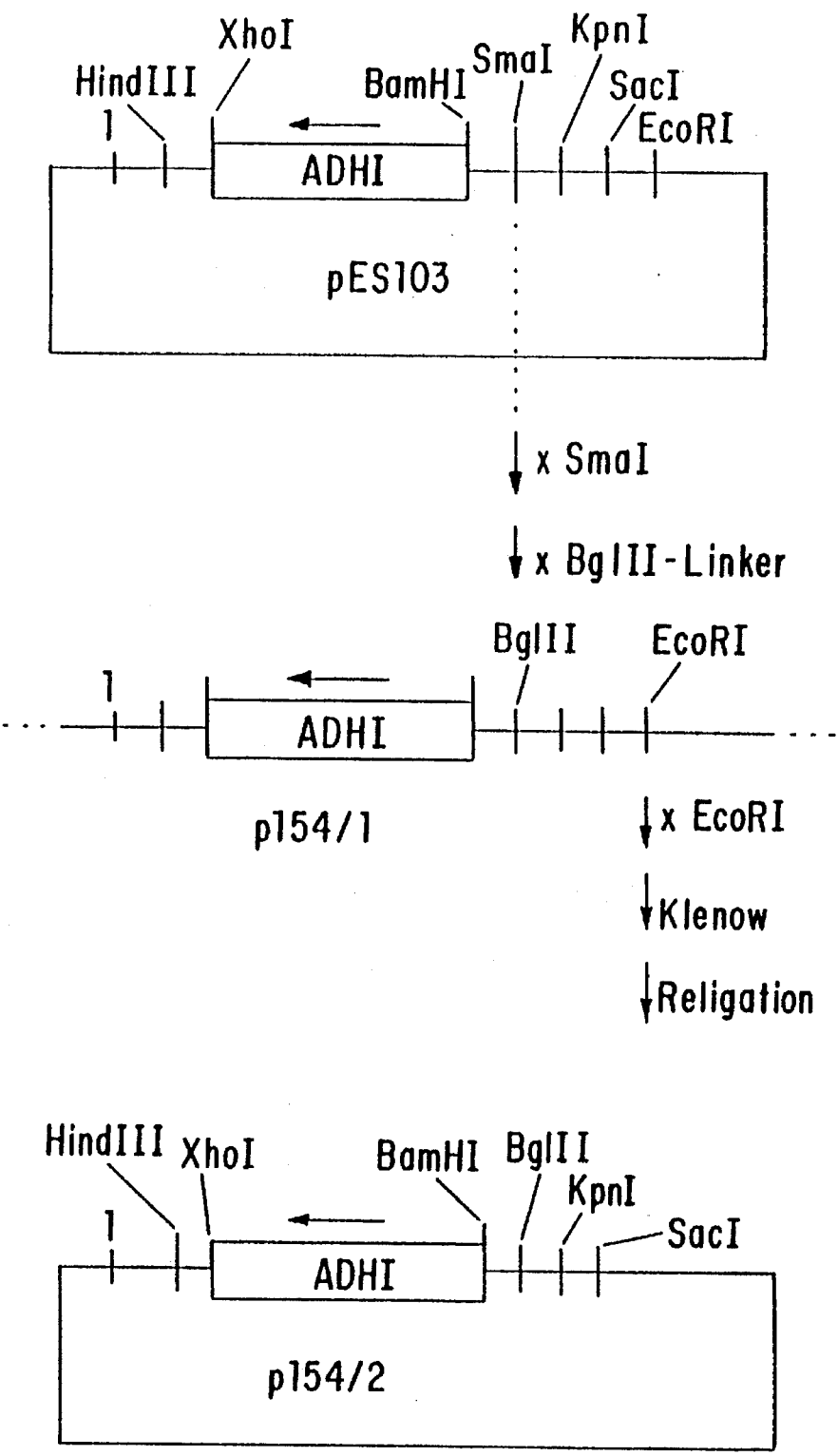

FIG. 6: Construction of plasmid p154/2 which contains the ADHI promoter as a 1500 bp BamHI/XhoI fragment.

FIG. 7: Construction of plasmid p150/2 with the units of ADHI promoter and ADHII terminator (336 bp XbaI/HindIII fragment) needed for the expression of hMn-SOD.

Figure 8:
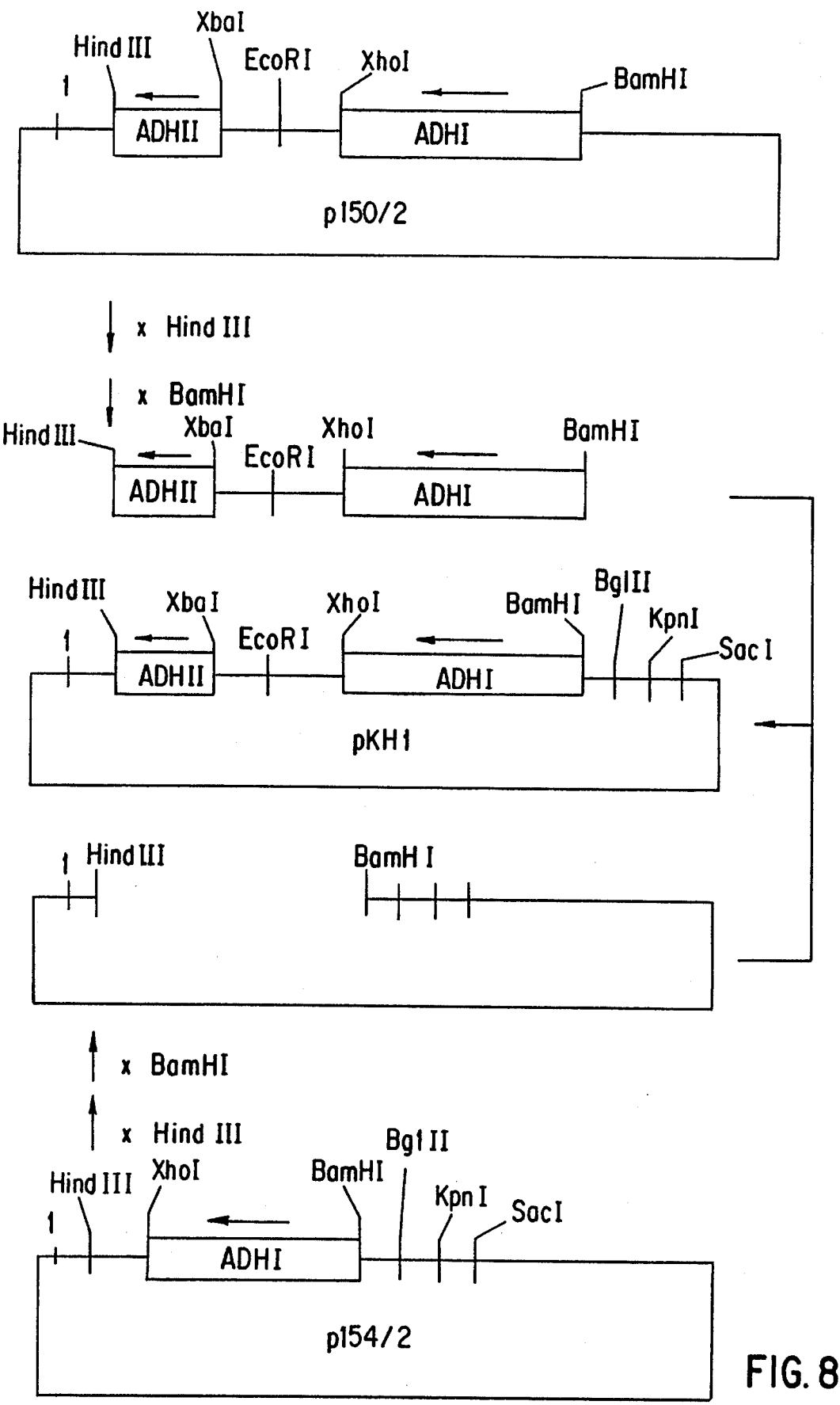

FIG. 8: Preparation of the final plasmids (pKH1 and pKH2) with the ADHI promoter or ADHIk promoter and the ADHII terminator, by further insertion of the hMn-SOD cDNA via the XhoI/EcoRI site. The plasmid pKH2 corresponds to pKH1 except that pKH2 contains the ADHIk promoter instead of the ADHI promoter.

Figure 9:
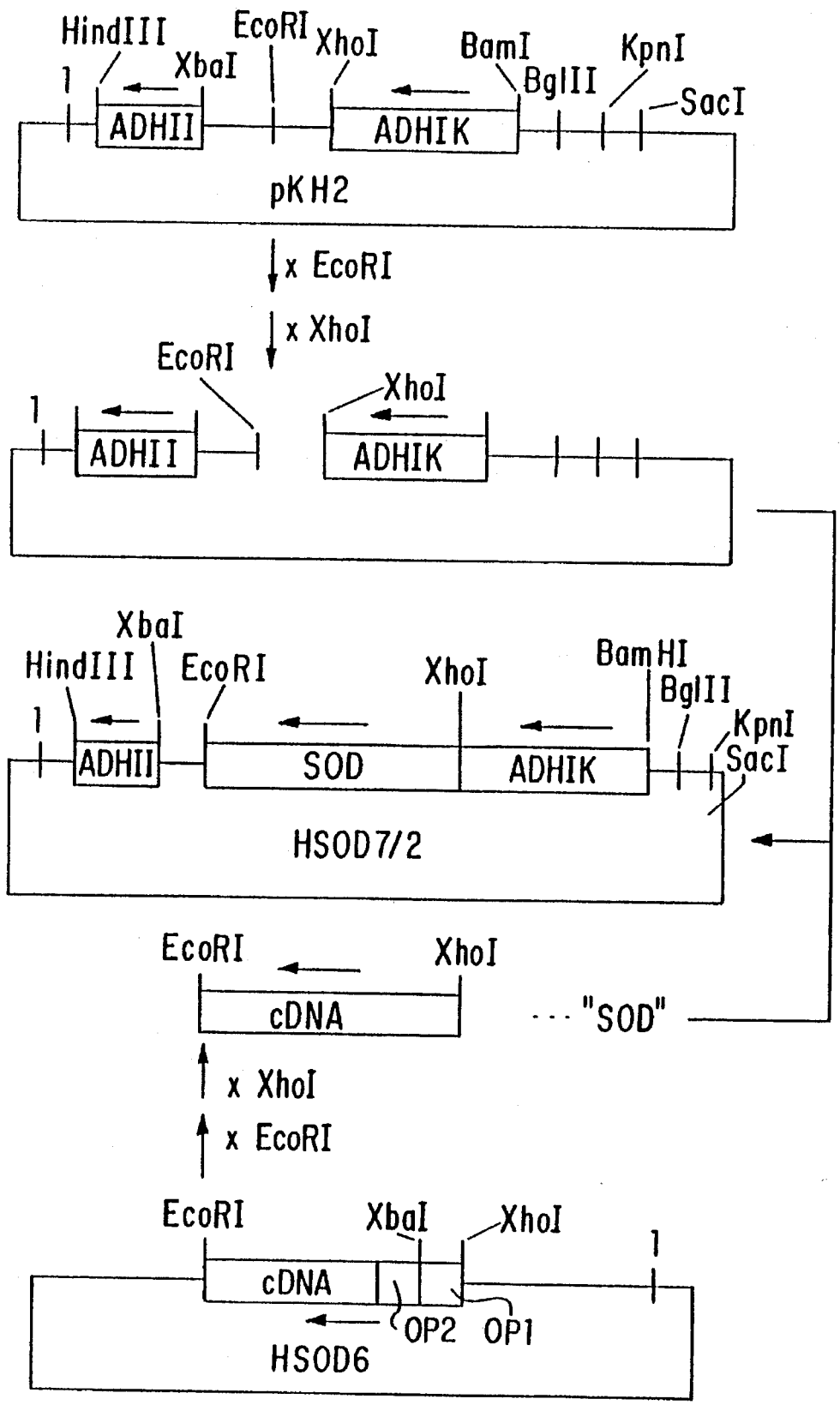

FIG. 9: Construction of the expression cassette HSOD7 with the shortened, approximately 400 bp long ADHI promoter (ADHIk). Construction with the ADHI promoter of the original length is effected starting from pKH1 in analogous manner.

FIG. 10: Construction of plasmids with the URA3 gene located inside the yeast Mn-SOD gene as a marker in various orientations relative to the Mn-SOD gene (SODY7, SODY8) in order to prepare a yeast Mn-SOD mutant suitable for expression. The gene transplacement in the corresponding yeast strain (DBY747) was carried out with SODY7 and SODY8.

Figure 11:
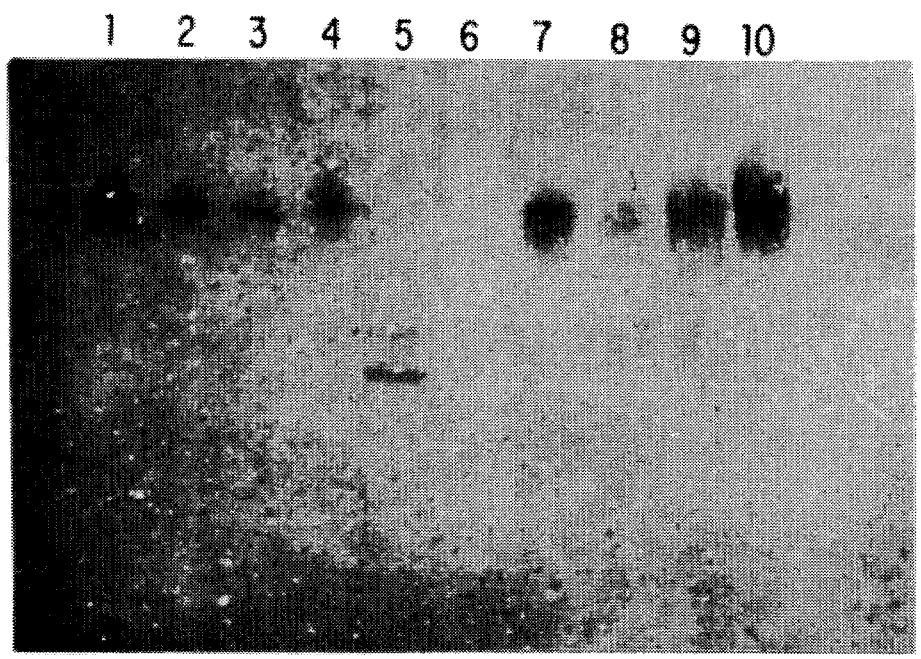

FIG. 11: Detection, by gel electrophoresis, of the expression of hMn-SOD via plasmids pWS490A and pWS491A in the yeast strain WS30-5g. Track 1: WS30-5g/pWS490A1, Track 2: WS30-5g/pWS490A2, Track 3: WS30-5g/pWS491A1, Track 4: WS30-5g/pWS491A2, Track 5: WS21-1(SOD1), contains yeast Mn-SOD, Track 6: WS30-5g, Tracks 7 to 10: hMn-SOD from liver (0.3 mcg Track 8, 1.2 mcg Track 9, 3.0 mcg Track 10). The numbers 1 and 2 following the names of the plasmids indicate different transformants with the same plasmids.

Figure 12:
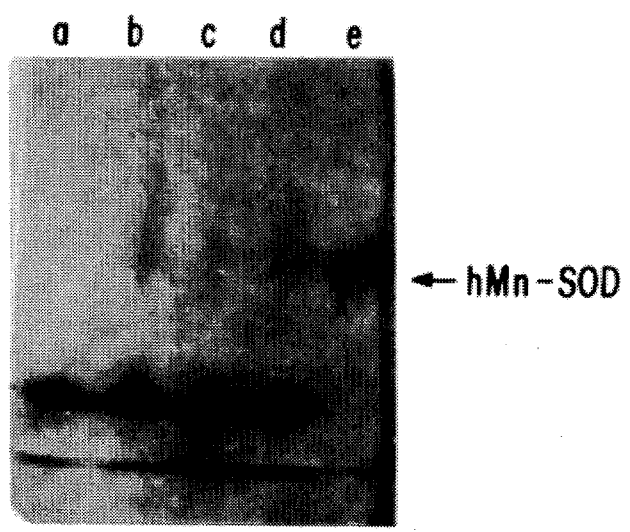

FIG. 12: Analysis of the Mn-SOD activity in yeast extracts which contain the expression plasmids pEO24-AB, pEO25-AC and pEO26-AC, separating the proteins in polyacrylamide gel and subsequently staining their activity with o-dianisidine by known methods: a=WS30-5g, b=WS30-5g/pEO24-AB, c=WS30-5g/pEO25-AC, d=WS30-5g/pEO26AD, e=marker (0.15 mcg human liver Mn-SOD).

Figure 13:
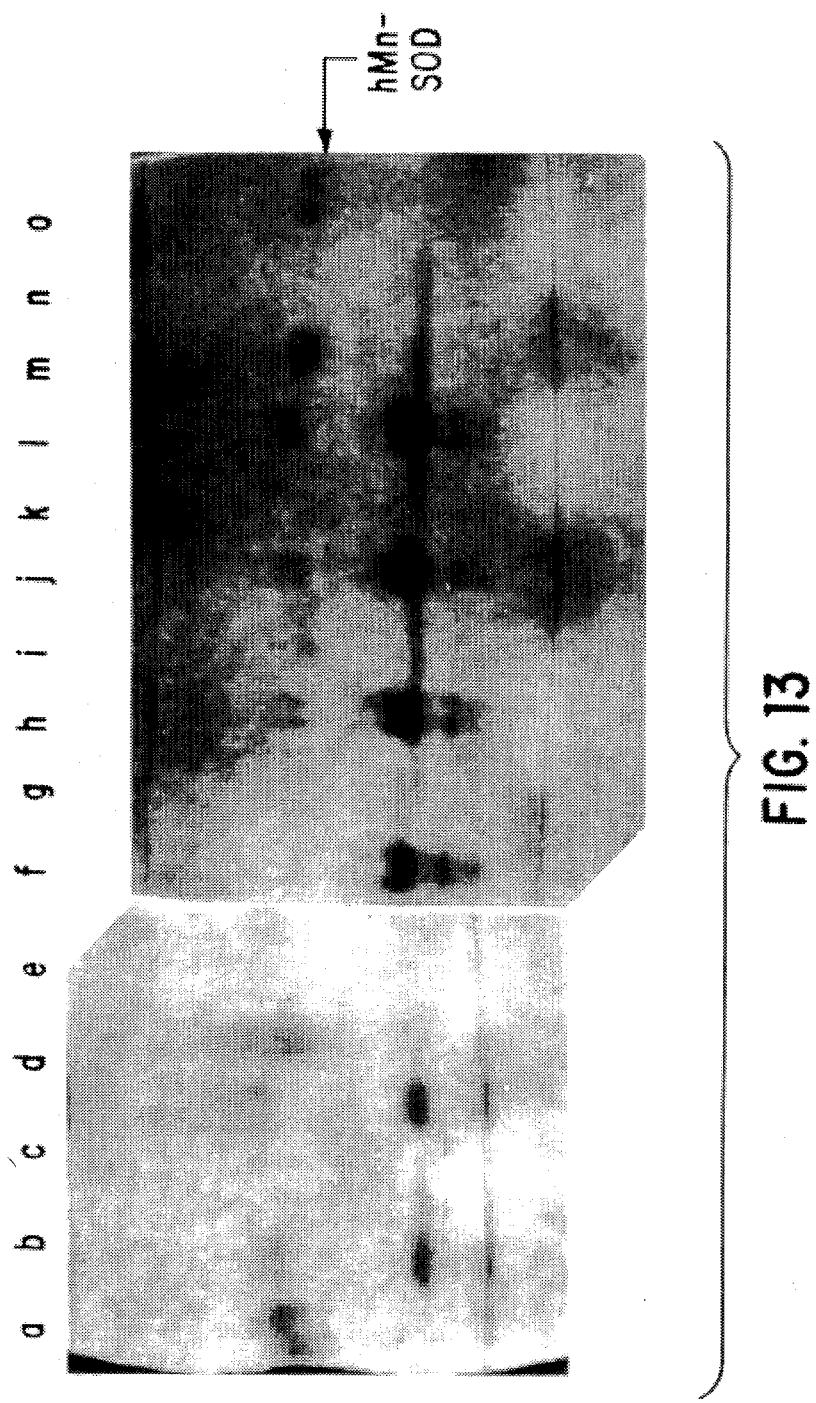

FIG. 13: Analysis of the activity of recombinant human Mn-SOD in the mitochondria or in the cytoplasm of 6 different yeast transformants, by gel-electrophoretic separation of the protein and subsequent activity staining with o-dianisidine by known methods (CP-Extr.=cytoplasm extract, MC-Extr.=mitochondria extract):

a=marker, 0.15 mcg human liver Mn-SOD
b=CP-Extr. WS30-5g pWS490A without MC-leader
c=MC-Extr. " " "
d=CP-Extr. " pEO24-AB with MC-leader
e=MC-Extr. " " "
f=CP-Extr. " pWS491A without MC-leader
g=MC-Extr. " " "
h=CP-Extr. " pEO25-AC with MC-leader i=MC_Extr. " " "
j=CP-Extr. " pWS550A without MC-leader
k=MC-Extr. " " "
l=CP-Extr. " pEO26-AD with MC-leader
m=MC-Extr. " " "
n=free trace
o=marker, 0.075 mcg human liver Mn-SOD FIG. 14: Elution diagram (Example 15, Step 5) of the chromatography of the hMn-SOD according to the invention after precipitation with $(NH_4)_2SO_4$ (Example 15, Step 4) using a Mono S cation exchange column (Pharmacia).

Figure 15:
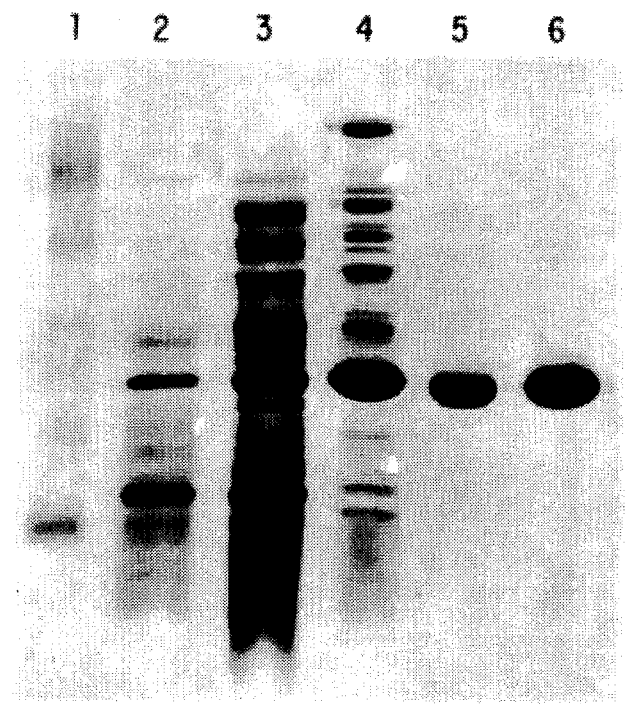

FIG. 15: SDS polyacrylamide gel (15%, silver colouration) of hMn-SOD probes after various purification stages.

1=4 mcl of marker (LMW-Pharmacia) 1:50
2=10 mcg crude extract
3=10 mcg after ammonium sulfate precipitation
4=9 mcg after chromatography on Mono S
5=1.5 mcg after chromatography on
6=5 mcg hydroxylapatite The following examples, which are not intended to restrict the invention, illustrate the invention in detail.

Materials used:

Unless otherwise stated in the Examples which follow, the following materials, solutions, plasmids, vectors and microorganisms are used:

ADHI promoter: DSM 4013 (pES103), deposited on (1500 bp BamHI/XhoI) 27.2.87

ADHI promoter, abbreviated to: DSM 4016 (pWS323E), filed on 27.2.87 (400 bp BamHI/XhoI)

ADHII terminator: DSM 4014 (pGD2), deposited on (336 bp XbaI/HindIII) 27.2.87

BamHI buffer: 150 mM NaCl, 6 mM Tris-HCl. pH 7.9, 6 mM $MgCl_2$, 100 mcg/ml BSA

Core buffer: 50 mM Tris-HCl pH 8.0, 10 mM $MgCl_2$, 50 mM NaCl

Denaturing solution: 0.5M NaOH, 1.5M NaCl

Denhardt solution: 1 g polyvinylpyrrolidone, (50×) MW 360,000, 1 g Ficoll, 1 g bovine serum albumin (BSA) ad. 100 ml $H_2O$.

E. coli C600: F⁻, supE44, thi1, thr1, leuB6, lacY1, tonA21, λ⁻ (ATCC 23724)

E. coli JM101: supE, thi, Δ(lac-pro AB), [F', traD36, proAB lacI$^q$Z, ΔM15]

High buffer: 100 mM NaCl, 50 mM Tris-HCl pH 7.5, 10 mM $MgCl_2$, 1 mM Dithiothreitol (DTT)

HincII buffer: 10 mM Tris-HCl pH 7.5, 60 mM NaCl, 10 mM MgCl, 1 mM 2-mercaptoethanol, 100 mcg/ml BSA Hybridising solution: like pre-hybridising solution but without salmon sperm DNA Klenow reaction 22 mcl DNA/$H_2O$, 2.5 mcl 10× solution: NTR buffer (0.5M Tris-HCl pH 7.2, 0.1M $MgSO_4$, 1 mM DTT, 500 mcg/ml BSA) per 1 mcl 2 mM dATP dGTP dCTP dTTP 2.5 U Klenow fragment (0.5 mcl)

Lambda buffer: 100 mM Tris-HCl pH 7.5, 10 mM $MgCl_2$, 1 mM EDTA

LB agar: LB liquid medium, 15 g/l Bacto-Agar (Difco)

LB liquid medium: 10 g/l Bacto-Tryptone (Difco), 5 g/l yeast extract (Difco); 5 g/l NaCl, 10M NaOH ad. pH 7.4

Ligation solution: 66 mM Tris-HCl pH 7.6, 10 mM $MgCl_2$, 5 mM DTT, 1 mM ATP 1U T4-DNA ligase Neutralising solution: 0.5M Tris-HCl pH 7.5, 1.5M NaCl Nitrocellulose filter: Schleicher & Schuell, membrane filter BA 85

NruI buffer: 50 mM KCl, 50 mM NaCl, 50 mM Tris-HCl pH 8.0, 10 mM $MgCl_2$

Prehybridising 5×SSC, 5×Denhardt solution, solution: 50 mM Na-phosphate buffer pH 6.8, 1 mM $Na_2P_4O_7$, 100 mcM ATP, 0.1% SDS, 30-100 (50) mcg/ml denatured, ultrasound-treated salmon sperm DNA pUC18: Pharmacia pURA3: DSM 4015, deposited on 27.2.87

S. cerevisiae DBY747: a, leu2, his3, trp1, ura3 (Yeast Genetic Stock Centre, Berkeley)

SC-URA medium: 0.67% BYNB (Difco), 2% glucose, 2% 50×AS mix (containing per liter: 1 g histidine, 6 g leucine, 2.5 g tryptophan, 4 g lysine, 1.2 g adenine, 2 g arginine, 1 g methionine, 6 g phenylalanine, 5 g threonine, 6 g isoleucine)

SmaI buffer: 10 mM Tris-HCl pH 8.0, 20 mM KCl, 10 mM $MgCl_2$, 10 mM 2-mercaptoethanol, 100 mcg/ml BSA SphI buffer: 10 mM Tris-HCl pH 7.5, 100 mM NaCl, 10 mM $MgCl_2$, 10 mM 2-mercaptoethanol, 100 mcg/ml BSA SSC (20×): 3.0M NaCl, 0.3M $Na_3$-citrate, pH 7.0

SSPE (20×): 3.6M NaCl 0,2M $Na_2HPO_4$, 20 mM EDTA, with NaOH (10N) ad. pH 7.4

TE buffer: 10 mM Tris-HCl pH 8.0, 1 mM EDTA

ThaI buffer: 50 mM Tris-HCl pH 8.0, 10 mM $MgCl_2$

Top agarose: LB liquid medium, 0.7% agarose (Seaken FM-agarose)

Prewash solution: 1M NaCl, 50 mM Tris-HCl pH 8.0, 1 mM EDTA, 0.1% SDS

EXAMPLE 1

Construction of a cDNA gene bank

Dice-sized pieces of fresh human placenta tissue were shock-frozen in liquid nitrogen and the tissue was powdered at below −80° C. The RNA was then extracted from the powdered tissue material using the procedure described by Chirgwin, J. M. et al. and then prepared (Chirgwin, J. M. et al., Biochemistry 18, 5294–5299, 1979).

The poly(A)⁺RNA was prepared from the resulting RNA using the method of Aviv, H. and Leder, P. (Proc. Natl. Acad. Sci. USA 69, 1409–1412, 1972). The cDNA was synthesised using a "cDNA synthesis system" (Amersham RPN 1256).

Packaging was carried out with Gigapack (vector cloning systems). All other procedural steps for cloning into the EcoRI site of λgt10 were carried out as prescribed by Huynh T. V. et al. (DNA Cloning Vol. 1, D. M. Glover ed., IRL Press, Chapter 2, 1985) except that E. coli C 600 was used as the "plating bacteria". The titre of the λgt10 phage representing the cDNA gene bank was $1.2×10^{10}$ pfu/ml, the number of independent clones $1×10^6$.

EXAMPLE 2

Amplification of the λgt10 gene bank

A suitable E. coli yeast strain (C600, genotype F-, supE44, thi1, thr1, leuB6, lacY1, tonA21, lambda(M. A. Hoyt et al., 1982, Cell 31, 5656) was pre-cultivated overnight at 37° in LB medium supplemented with 0.2% maltose.

This overnight culture was centrifuged for 5 min at 3000 rpm and suspended in ice cold 10 mM MgSO₄ solution so that the OD600 nm was 4.0. The Mg cells thus prepared were stored at 4° C. and could be used for a week.

12×200 mcl of Mg cells were mixed, in sterile test tubes, with a phage suspension (50000 pfu of the cDNA gene bank per plate) and incubated at 37° C. for 20 min. Then 6–7 ml of molten top agarose adjusted to a temperature of 42° C. (containing 10 mM MgSO₄, final concentration) were pipetted into each test tube, mixed and poured out onto 12 agar plates (13.5 cm in diameter) preheated to 37° C. with 10 mM MgSO₄ and the plates were incubated at 37° C. for 6–12 hours.

EXAMPLE 3

Primary screening to identify recombinant λ-phages a. Preparation of the nitrocellulose filters After incubation the plates thus prepared were cooled to 4° C. Nitrocellulose filters numbered with a pencil were placed on the surface of the plates and their positions on the plates were marked with pin pricks. About 1 min after being thoroughly wetted, the filters were carefully removed again, placed in denaturing solution and incubated for 1 min at room temperature (RT). They were then neutralised in neutralising solution for 5 min at RT and incubated for 30 sec in 2×SSPE, again at RT.

Up to 3 further extracts were prepared from each plate, with the filters being left on the plate 30 sec longer each time. The positions of the pin pricks were transferred accurately to the next filters.

The filters were dried in air, lying on filter paper, and the DNA was fixed at 80° C. by baking for 2 hours. The plates were kept until the results of the following hybridisation were obtained.

b. Preparation of the $^{32}$P-labelled probes

The synthetic oligonucleotide mixtures were prepared using a 381A DNA synthesiser (Applied Biosystems), purified by polyacrylamide gel electrophoresis (20% in 8M urea, T. Maniatis et al., Molecular Cloning, Cold Spring Harbor Laboratory, 1982, page 173 ff) and desalinated over Sephadex G50 (Pharmacia). The DNA probes thus synthesised are complementary to RNA base sequences which code a) for amino acids 39–46 or b) for amino acids 200–207 (D. Barra et al., Oxy Radicals and their scavenger Systems, Vol. 1, 336–339, 1983) and have the following base sequences:

Tris-HCl pH 7.6, 0.1M MgCl₂, 50 mM dithiothreitol, 10 units T4 polynucleotide kinase (BRL), water ad. 10 mcl.

The reaction lasted 60 min at 37° C. and was stopped by the addition of 25 mM EDTA. Any radioactivity not incorporated was removed by exclusion chromatography using a 1 ml Biogel P6-DG (Biorad) column produced in a 1 ml one-way syringe. TE buffer was used as eluant.

c. In situ hybridisation

In order to remove any residual agarose and bacteria from the nitrocellulose which will cause considerable background radiation during hybridisation, the filters were incubated in a sufficient volume of prewash solution at 65° C. whilst being tilted for a period ranging from some hours to overnight. In order to saturate non-specific binding sites for DNA on the nitrocellulose filters, these filters were incubated for 1–12 hours at 37° C. in the prehybridising solution which had earlier been degassed in vacuo.

The radioactively labelled DNAs used for hybridisation (about 1×10⁹ cpm/mcg) were added to the required quantity of degassed hybridising solution which was preheated to 37° C. In order to keep the concentration of the DNA probe as high as possible in the hybridising solution, only just enough hybridising liquid to keep the filters just covered with liquid was used. Hybridisation lasted for 12–18 hours at 37° C.

The nitrocellulose filters were then rinsed three times in 6×SSC and 0.05% SDS (4° C.) by the method of Wood et al, (Proc. Natl Acad Sci Vol 82, 1585–1588, 985) and similarly washed at 4° C. for 2×30 min. The filters where then rinsed three times at room temperature (RT) in a freshly prepared solution containing 3M tetramethylammonium chloride (Me4NCl), 50 mM Tris-HCl pH 8, 2 mM EDTA and 0.05% SDS, washed 2×30 min at RT and finally washed 3×30 min at 49° C. (oligonucleotide mixture a)) or at 52° C. (oligonucleotide mixture b)), dried in air (oligonucleotide mixture b)) and stuck to paper. X-ray films were exposed for 2–8 days at −70° C. using an "intensifying screen".

EXAMPLE 4

Plaque purification

Since no individual plaques could be isolated in the first search, with the high density of plaques used, the recombinant lambda phage were purified by several successive searches whilst the plaque density was simultaneously reduced. After development of the autoradiograms, regions were isolated from the agar plate (of 3 primary screenings carried out, of 28 regions, 2 were positive, of 35 regions 1 was positive and of 15 regions 5 were positive), which

|    |    |     |     | C   |    | C  |    | C  |    |     |     |     |    |
|----|----|-----|-----|-----|----|----|----|----|----|-----|-----|-----|----|
| a) | 5' | TG  | ITA |     | TT |    | TC |    | TC | IGT | IAC | ITT | 3' |
|    |    |     |     | T   |    | T  |    | T  |    |     |     |     |    |
|    |    |     |     |     | A  |    | C  |    |    | C   |     |     |    |
| b) | 5' | TC  | IGT | IAC |    | TT |    | TC | CCA|     | TT  | IAT | 3' |
|    |    |     |     |     | G  |    | T  |    |    | G   |     |     |    | wherein A, G, C and T represent the corresponding nucleotides and I represents inosine.

The chemically synthesised DNA probe mixtures were each dissolved in water at a concentration of 20 pM/mcl.

Reaction mixture:

20–100 pM gamma $^{32}$-PATP (>3000Ci/mmol, Amersham), lyophilised from ethanolic solution, 20–100 pmol oligonucleotide, 1 mcl 10×kinase buffer (0.7M yielded a positive hybridising signal on the two nitrocellulose filters which had been hybridised in duplicate. The desired site was pricked out of the agar using the sharp end of a sterile Pasteur pipette and transferred into 0.3–0.6 ml of lambda buffer (100 mM Tris-HCl pH 7.5, 10 mM MgCl₂ and 1 mM EDTA). However, SM buffer may also be used (Maniatis T., Molecular Cloning, 1982, page 70). After the addition of one drop of chloroform, the phages were left to diffuse out of the agar overnight at 4° C. and each individual phage suspension was plated out again in several dilutions. Another nitrocellulose filter was prepared from plates having 300–100 plaques and this extract was then hybridised against both DNA probes. This procedure was repeated, and individual plaques were followed up, until all the plaques on a plate gave a positive hybridisation signal.

EXAMPLE 5

Analysis of the phage clones obtained a. Titration of λ-phage

The phage suspensions were diluted with lambda buffer in dilution steps of 1:10, mixed by tilting several times, and plated out. After incubation at 37° C. the plaques formed on the bacterial lawn were counted and the titre (plaque forming units (pfu)) was determined. The titre for the purified phage suspensions was 2.2–8.6×10$^{10}$ pfu/ml.

b. Preparation of lambda phage DNA

After isolation and titration of the inherently homogeneous phage clones, they were plated in a density of 2×10$^6$ pfu/13.5 cm of Petridish (with culture medium of composition: 1.5% agarose, 10 g/l tryptone, 5 g/l yeast extract, 5 g/l NaCl, 10 mM MgSO$_4$ and 0,2% glucose) with 200 mcl of C600Mg cells (4 OD$_{600}$), incubated for 5 hours at 37° C. and then cooled to 4° C. Elution of the phage was effected by covering the plates with 8 ml of lambda buffer and a few drops of chloroform and tilting gently at 4° C. overnight. The supernatant purified by centrifuging (15000 rpm, 15 min, 4° C.) was finally removed and the phage were pelleted by centrifuging at 50000 rpm (Beckman Ti50 rotor) for 30 min at RT. After the addition of 500 mcl of lambda buffer and incubation with ribonuclease A (RNase A, 10 mcg/ml) and deoxyribonuclease (DNase, 1 mcg/ml), for 30 min at 37° C., the salt concentration was increased by the addition of 23 mcl of 0.5M EDTA, 12 mcl of 1M Tris-HCl pH 8.0 and 6.5 mcl of 20% SDS and the enzymes present were deactivated by incubating at 70° C. for 15 min. After extracting once with phenol and twice with chloroform/isoamyl alcohol (24:1) in equal volumes the DNA was precipitated by the addition of 0.1 vol. 3M sodium acetate, pH 5.2, and 2 vol. of alcohol, then centrifuged off, washed with 70% alcohol, dried and taken up in 50 mcl of TE buffer.

c. Restriction analysis 2 mcl of DNA solution were incubated with 5 units of EcoRI in HIGH buffer for 2 hours at 37° C., the fragments obtained were separated on a 1% agarose gel (T. Maniatis et al., 1982, p149ff) under a voltage of 1–5 volts per cm, the fragments with lengths ranging from 500 to 1000 base pairs were eluted from the gel (G. M. Dretzen et al., Anal. Biochem. 112, 295–298, 1981) and finally subjected to sequence analysis.

d. Sequence analysis

Subcloning of the restriction fragment into a vector (Bluescribe M13+ or M13–, vector cloning systems (C. Yanisch-Perron et al., Gene 33,103–119, 1985)) suitable for sequence determination according to Sanger (F. Sanger et al., Proc.Natl. Acad.Sci. 74, 5463–5467, 1977; F. Sanger et al., FEBS-Letters 87,107–111, 1978) was carried out by the usual methods for effecting the restriction and ligation of DNA fragments and transformation of E. coli host cells (T. Maniatis et al., 1982, Molecular Cloning, Cold Spring Harbor Press, p104, 146ff, 396; DNA-Cloning, IRL-Press 1985, Vol. 1, chapter 6). In this way 100 ng of isolated EcoRI-cDNA fragments were inserted, via EcoRI sites, into the correspondingly prepared dsDNA form (replicative form, 50 ng) of the vector (by incubation for 2 to 12 hours at 14° C. in 10 mcl of ligation solution) and with this recombinant construction (entitled BS3, BS5, BS8, BS9, BS12, BS13, BSXIII) competent E. coli cells (strain JM 101) were transformed. The single strand DNA of the recombinant phages was isolated and sequenced according to Sanger. The sequences read were processed using suitable computer programs (R. Staden, Nucl. Acid. Res. 10, 4731–4751, 1982). The isolated clone 8 (BS8) contains the coding sequence from amino acid 22 of the mature enzyme (FIG. 1).

EXAMPLE 6

Construction of an expression cassette

In order to express the hMn-SOD in yeast, it is necessary to complete the isolated cDNA and to construct an expression cassette, the ADHI promoter being used in its original length (about 1500 bp, Methods in Enzymology, Vol. 101, Part C, 192–201, 1983), in shortened form (ADHIk about 400 bp) and the ADHII terminator (Dr. R. Beier and E. T. Young, Nature 300, 724–728, 1982) being used as well.

a. Completion of the gene

Since the isolated cDNA clone 8 lacks the bases corresponding to the 21 amino acids (AA) at the N terminus, in order to complete the gene according to the reported amino acid sequence (D. Barra et al., J. Biol. Chem. 25.9, 12595–12601, 1984) taking into account the yeast codon selection (P.M. Sharp et al., Nucl.Acids.Res. 14, 5125–5143, 19S6) 2 pairs of oligonucleotides were constructed and synthesised (381A DNA synthesiser, Applied Biosystems) as the XhoI-XbaI fragment (OP1, corresponding to formula VIa) or the XbaI-NcoI fragment (OP2, corresponding to formula rib). OP1 was inserted via XhoI/XbaI into the plasmid V 17 (obtained from pUC18 (J. Vieira and J. Messing, Gene 19, 259, 1982) after HincII restriction and insertion of XhoI linkers (New England Biolabs, d(CCTC-GAGG) and SmaI restriction of the resulting plasmid pES102 with subsequent insertion of NcoI linkers (New England Biolabs, d(CCCATGGG)) (FIG. 2), whilst OP2 was inserted via XbaI/NcoI. In order to do this, 4 mcg of V 17 DNA were digested with 10 units of XbaI and NcoI or XhoI and XbaI in 40 mcl of CORE buffer for 2 hours at 37° C. and purified by gel electrophoresis (0.7% agarose, see above). 5 mcl portions of the synthesised single strands of OP1 or OP2 (10 pM/mcl in each case) were mixed together, incubated for 10 minutes at 65° C. and slowly cooled to RT. 1/10 thereof was ligated with 50 ng of doubly cut vector (XhoI/XbaI for OP1 and XbaI/NcoI for OP2) under the conditions described above (plasmids HSOD2 and HSOD3, FIG. 2). Finally, HSOD2 and HSOD3 were combined to form plasmid HSOD4 via ScaI/XbaI (i.e. after double digestion with ScaI and XbaI in CORE buffer for 2 hours at 37° C.) after purification and isolation of the cut vectors by gel electrophoresis and ligation under the conditions described above (cloning of the oligo pairs OP1 and OP2) (FIGS. 2, 3). This plasmid HSOD4 was prepared to receive the ThaI/EcoRI cDNA fragment by NcoI restriction, followed by Klenow fill-in and EcoRI restriction: 5 mcg of DNA were incubated for several hours at 37° C. in 50 mcl of high buffer with 18 units of NcoI, the cut DNA was purified by gel electrophoresis, then isolated and half of it was incubated in 30 mcl of Klenow reaction solution for 1 hour at RT.

After the reaction had been ended by the addition of 2 mcl of 0.5M EDTA and the reaction solution had been incubated at 70° C. for 10 minutes the DNA was purified by gel electrophoresis, isolated and re-cut with 7.5 units of EcoRI in 20 mcl of HIGH buffer, purified again and isolated. (FIG. 5)

The ThaI/EcoRI cDNA fragment was prepared as follows:

Competent E. coli host cells (strain JM 101) were transformed with the plasmid BS8 which contains the isolated cDNA clone 8 (see above) and the plasmid was prepared under suitable conditions (T. Maniatis et al., 1982, page 368).

After restriction with ThaI (10 mcg of plasmid were digested in 40 mcl of ThaI buffer with 25 units of ThaI for 8 hours at 60° C.), recutting the 759 bp ThaI fragment with EcoRI (see above), followed by purification by gel electrophoresis and isolation of the corresponding fragment, the ThaI/EcoRI fragment thus obtained (FIG. 4) was combined with the correspondingly prepared plasmid HSOD4 to form HSOD6 (FIG. 5) (about 100 ng of fragment were ligated with 50 ng of cut vector in 10 mcl of ligation solution (see above)). Plasmid HSOD6 thus contains the complete cDNA for hMn-SOD including Met. The reading frame is retained.

b. Construction of the expression cassette

Plasmid HSOD6 was doubly digested with XhoI and EcoRI (5 units/mcg of DNA) in CORE buffer, the XhoI fragment (gene) was isolated and inserted into the plasmid PKH1 or PKH2 via XhoI/EcoRI. The plasmids PKH1 and PKH2 were prepared as follows (FIGS. 6, 7, 8): after SinaI restriction (1 mcg of plasmid was digested with 5 units of SmaI in SmaI buffer for 2 hours at 37° C.), purification and isolation, BglII linkers were inserted in plasmid PES 103, which contains the ADHI promoter as a 1500 bp BamHI-XhoI fragment in PES 102 (PES 102 is a pUC18 derivative which contains in the HincII cutting site an XhoI linker, the construction of the BamHI-XhoI fragment being described in "Methods in Enzymology" 101, 192–201) (T. Maniatis et al., 1982, page 396). The plasmid thus obtained (P154/1, FIG. 6) was changed into plasmid 154/2 by EcoRI restriction (see above), Klenow fill-in (see above) and religation (1 mcg of DNA was incubated in 40 mcl of ligation solution (see above) overnight at 14° C.) (FIG. 6).

Also starting from plasmid pES103, the linker -XhoI.EcoRI. XbaI.HindIII- (FIG. 7, synthesised using a 381A DNA synthesiser) was inserted after double digestion with XhoI and HindIII in CORE buffer. This linker contains the sequence

```
TCGAGGAATTCTCTAGAA
    CCTTAAGAGATCTTTCGA.
```

The ADHII terminator was inserted in the resulting plasmid 150/1 via XbaI/HindIII (double digestion in CORE buffer) (plasmid 150/2 (FIG. 7)). The ADHII terminator was obtained as follows: plasmid pMW5 ADHII (Washington Research Foundation) was digested with HindIII (core buffer) then with SphI (in SphI buffer) and the isolated 605 bp fragment was cloned into the vector V18 and an XbaI linker (Biolabs, CTCTAGAG) was incorporated in the HincII cutting site (for ligation see above). A 335 bp long XbaI/SphI fragment was ligated into pUC18 (XbaI/SphI) (pGD2).

The vector V18 was obtained by incorporating a HindIII linker in pUC18 in the SmaI site and the. HindIII site is missing from its original location, so that the multicloning site in V18 runs as follows: EcoRI.SstI.KpnI.HindIII.BamHI.XbaI.SalI.PstI.SphI Finally, after double digestion with XbaI/HindIII in CORE buffer the ADHII terminator was isolated by the usual methods (see above). Plasmid 150/2 thus contains the units necessary for gene expression, apart from the gene which is to be inserted via XhoI/EcoRI, namely approximately 1500 bp (promoter), 7 bp (XhoI linker), 6 bp (EcoRI linker), 7 bp (XbaI linker), 329 bp (terminator). These units were then inserted into the vector 154/2 (FIG. 8) via BamHI/HindIII (double digestion in CORE buffer). In the resulting plasmid PKH1 (FIG. 8) the ADHI promoter was analogously replaced by the shortened promoter ADHIk as the BamHI/XhoI fragment (412 bp) (pKH2, FIG. 9).

Finally, the complete cDNA gene (see above) cut out of HSOD6 was inserted into plasmids via XhoI/EcoRI (see above). The resulting plasmids HSOD7/1 and HSOD7/2 (FIG. 9 shows only HSOD7/2) differ from one another only in the different promoters ADHI and ADHIk (see above). The expression cassettes thus prepared were inserted into the correspondingly prepared and freely obtainable yeast transformation vectors YEp13 (J. R. Broach et al., Gene 8, 121–133, 1979, ATCC 37115), pJDB207 (DSM 3181, deposited on 28.12.84), pEAS102 (see above), YIp5 (K. Struhl et al., Proc. Natl. Acad. Sci. USA 76, 1035–1039, 1979, ATCC 37061) via the cutting sites BamHI and HindIII, via BglII/HindIII (after double digestion the plasmids in CORE buffer and isolation of the expression cassettes cut out).

EXAMPLE 7

Preparation of a yeast Mn-SOD mutant suitable for expression

The gene for yeast Mn-SOD (A.P.G.M. van Loon et al., Gene 26, 261–272, 1983) is contained as a BamHI fragment in the vector PL 41 (FIG. 10) and the sequence has been published in full (C.A.M. Marres et al., Eur.J.Biochem. 147,153–161, 1985). After restriction with BamHI (2 mcg plasmid were digested with 5 units in 150 mM NaCl 6 mM Tris-HCl pH 7.9, 6 mM $MgCl_2$, 100 mcg/mcl bovine serum albumin for 2 hours at 36° C.) the 2045 bp long BamHI fragment which contains the gene was purified as usual by gel electrophoresis and isolated and subcloned via BamHI into the vector VO (pUC18, but with no HindIII cutting site).

The vector VO was obtained by cutting 1 mcg of pUC18 with HindIII (CORE buffer), isolating the linearised fragment from the gel by known methods, filling in the projecting ends with 2 U Klenow polymerase (ligase buffer +0.2 mM dNTP) and religating after 20 minutes at RT by the addition of 2 U T4-DNA ligase overnight at 14° C.

The plasmid SODY1 (FIG. 10) was purified by NruI restriction (1 mcg of plasmid were digested with 5 units of NruI in NruI buffer for 2 hours at 36° C.) by gel electrophoresis and changed to SODY3 (FIG. 10) by the insertion of a HindIII linker (CAAGCTTG) (FIG. 10). Finally, the URA3 gene (obtained from pURA3) was inserted into the HindIII cutting site: 4 mcg of SODY3 were digested with 20 units of HindIII for 2 hours at 37° C. in CORE buffer and dephosphorylated: 40 mcl of $H_2O$, 10 mcl of 1 mM EDTA, 5 mcl of 1M Tris-HCl pH 9.5, 1 mcl of 100 mM spermidine, 1 mcl of calf intestinal alkaline phosphatase (CIAP, 1 mg/ml $H_2O$) were added to 40 mcl of digestion mixture and the whole was incubated at 36° C. After 15 minutes, a further 1 mcl of CIAP were added and the mixture was incubated for another 15 minutes. The dephosphorylated vector was also purified by agarose gel electrophoresis. 2 mcg of plasmid pURA3 were cut with HindIII (see above) and a 1.2 kb fragment which contains the yeast gene URA3 was also isolated and inserted into the prepared vector (see above).

The resulting plasmids SODY7 and SODY8 contain the URA3 gene within the yeast Mn-SOD gene and differ in the orientation of the URA gene relative to the Mn-SOD gene (FIG. 10).

The orientation of the URA3 gene relative to the Mn-SOD gene can be determined, since the URA3 gene contains an asymmetric PstI site.

A "gene transplacement" was carried out (Methods in Enzymology 101, 202–211 and 211–228) with the plasmid SODY7 and SODY8 in the strain DBY 747 (genotype a, leu2, his3, trp1, ura3, Yeast Genetic Stock Centre, Berkeley). The strain DBY 747 was transformed with the BamHI fragment from SODY7 and SODY8 (J. D. Beggs, Nature 275, 104, 1978). To do this, 20 mcg of SODY7 or SODY8 were cut with 50 U BamHI in 200 mcl of BamHI buffer (150 mM NaCl, 6 mM Tris-HCl pH 7.9, 6 mM $MgCl_2$, 1 mM DTT) and the entire digestion mixture (without separating off the pUC portion) was extracted with phenol (Maniatis, T. et al., Molecular Cloning, 1982, page 458ff) and concentrated by ethanol precipitation (addition of 20 mcl of 3M sodium acetate pH 5.5, 500 mcl of ethanol). The DNA was taken up in 10 mcl of water and used directly for the transformation of yeast.

The transformants were selected for uracil prototrophy.

Individual transformants were cultivated overnight in 5 ml of SC-URA medium at 28° C. The cells were harvested by centrifuging, broken by the method of van Loon et al. (Proc.Natl.Acad.Sci. USA 83, 3820–3824, 1986) and tested for their content of Mn-SOD. The measurement of Mn-SOD and Cu/Zn-SOD by gel electrophoresis were carried out by existing methods (Ch. Beauchamp and I. Fridovich, Anal. Biochem. 44, 276–287, 1971; H. P. Misra and I. Fridovich, Arch.Biochem.Biophys. 183, 511–515, 1977; B. J. Davis, Annals of the NY Academy of Sciences Vol. 121, 404–427, 1964). The method which proved best was the separation of the proteins followed by negative staining with nitroblue tetrazolium (B. J. Davis, 1964; Ch. Beauchamp and I. Fridovich, 1971). It is possible to increase the sensitivity by staining with dianisidine (H. P. Misra and I. Fridovich, 1977). A spectrophotometric assay (Hyland, K. et al., Anal. Biochem. 135. 280–287, 1983) with alkaline dimethylsulphoxide as the $O_2^-$ generating system and with cytochrome c as "scavenger".

Mn-SOD on the one hand and Cu/Zn-SOD on the other hand are distinguished by the addition of KCN (see above and M. Ysebaert-Vanneste and W. H. Vanneste, Anal.Biochem. 107, 86–95, 1980). The strains SODY7/2, SODY7/6 SODY7/8 and SODY7/10 contained no Mn-SOD activity.

EXAMPLE 8

Preparation of the expression vectors

The expression cassettes described in Example 6b were cut out of the plasmids HSOD7/1 and HSOD7/2, respectively, as BglII/HindIII fragments (in each case, 2 mcg of plasmid DNA in the CORE buffer, 2 hours at 37° C. with 10 U of enzyme). Similarly, 1 mcg of YEp13, pJDB207 and pEAS102 were each cut with HindIII-BamHI (digestion conditions as described above).

50 mcg of vector DNA and 200 mcg of insert were ligated in ligase buffer (as described) with 1 U ligase overnight at 14° C. and used to transform the *E. coli* strain HB101. The following Table contains the names of the corresponding plasmids.

TABLE 1

Names of the expression vectors

| Vector | Insert: HSOD7/1 | HSOD7/2 |
|---|---|---|
| YEp13 | pWS550A | pWS371A |
| pJDB207 | pWS490A | pWS372A |
| pEAS102 | pWS491A | pWS373A |

EXAMPLE 9

Preparation of a yeast strain (WS30–5g) suitable for transformation

A yeast strain was prepared which contains, in addition to the genetic markers described for the yeast strain SODY7/2, a mutation in one of the lysosomal chief proteases (which can activate other lysosomal proteases by their activity) and thus releases fewer proteases when the yeast cells are broken up (mutation pep4) (E. W. Jones et al., Genetics 102, 665-677, 1982).

The Mn-SOD-deficient strain SODY7/2 was crossed with the protease-deficient strain WS20-25 (α leu2 his3 trp1 ura3 pep4) and the resulting haploids were investigated for their genetic markers (F. Sherman et al., Methods in Yeast Genetics, Cold Spring Harbor, N.Y., 1972).

The resulting strain WS30-5g (leu2 his3 trp1 pep4 sod1) is readily transformable and fulfills the desired conditions.

Such crossing may also be carried out with equally good results with other well known and easily obtainable yeast strains, for example with 20 B-12 (Yeast Genetic Stock Center, Berkeley).

EXAMPLE 10

Yeast transformation and expression in yeast

The yeast strain SODY7/2 was transformed with the plasmids pWS371A, pWS372A and pWS373A (J. D. Beggs, Nature 275, 104–109, 1978) and the transformants were investigated for their expression.

To achieve this, a pre-culture of the transformants was prepared in SC-Leu liquid medium (analogous to the SC-URA medium described, except that it additionally contains 2.4 g of uracil but no leucine) (shaking at 300 rpm at 28° C. overnight). 100 mcl thereof were inoculated into 4 ml of YP5%D (1% Bacto yeast extract, 2% Bacto peptone, 5% glucose) and cultivated overnight (like the pre-culture). The cells were harvested and broken as already described in Example 7. The quantity of crude cell juice corresponding to 1 ml of culture was transferred to the activity gel. The activity test was carried out as described in Example 7.

The yeast strain WS30-5g (leu2 his3 trio1 pep4 sod1) was transformed with the plasmids pWS550A, pWS490A, pWS491A. The preparation of the pre-culture and culture and the measurement of the hMn-SOD activity were carried out as described above.

The expression of the plasmids pWS490A, pWS491A in yeast strain WS30-5g is documented by FIG. 11.

The quantity of MnSOD measured in the yeast under these conditions corresponded to approximately 0.5 mg/liter of culture.

EXAMPLE 11

Synthesis of a linker containing the yeast leader DNA sequence

Six different oligonucleotides EBI 656, EBI 636, EBI 643, EBI 646, EBI 660 and EBI 638 of the following sequences and lengths

| | |
|---|---|
| EBI 656: | |
| 5'TCGAGTATACAATGTTCGCGAAAACAGCTGCAGCTAATTTA3' | 41 bp |
| EBI 636: | |
| 5'TCTTGGTTAAATTAGCTGCAGCTGTTTTCGCGAACATTGTATAC3' | 44 bp |
| EBI 643: | |
| 5'ACAAGAAGGGTGGTTTGTCATTGCTCTCCACCACAGCAAGGAGAACC3' | 48 bp |
| EBI 646: | |
| 5'AGTGCTTGGTTCTCCTTGCTGTGGTGGAGAGCAATGACAAACCACCCT3' | 48 bp |
| EBI 660: | |
| 5'AAGCACTCTTTGCCAGACTTGCCATACGACTACGGTGCT3' | 39 bp |
| EBI 638: | |
| 5'CTAGAGCACCGTAGTCGTATGGCAAGTCTGGCAAAG3' | 36 bp | were prepared using a 381 A DNA synthesiser (Applied Biosystems), as described in 3b.

The oligonucleotides EBI 636, EBI 643, EBI 646 and EBI 660 were phosphorylated for the subsequent ligase reaction at their 5' ends under the following conditions:

Reaction mixture No. 1 2 mcl EBI 636 (=100 pmol) 1 mcl 10× linker kinase buffer 3 mcl 10 mM ATP 1 mcl T4 polynucleotide kinase, Biolabs 10U/mcl 3 mcl of water Reaction mixture No. 2 Analogous to No. 1 but with 2 mcl (100 pmol) of EBI 660

Reaction mixture No. 3 2 mcl oligonucleotide EBI 643 (=100 pmol) 2 mcl oligonucleotide EBI 646 (=100 pmol) 1 mcl 10×linker kinase buffer 3 mcl 10 mM ATP 1 mcl T4 polynucleotide kinase (10 units) 1 mcl water 10×linker kinase 0.7M Tris-HCl pH 7.6 buffer: 0.1M MgCl$_2$ 0.05M DTT (dithiothreitol)

The reaction lasted 30 minutes at 37° C. The T4 polynucleotide kinase was then deactivated by heating to 100° C.

The oligonucleotides EBI 656 and EBI 638 which are intended to form the 5' ends of the finished 128 bp long DNA insert (formula XI) were not phosphorylated in order to avoid the formation of multimeric DNA inserts in the subsequent ligase reaction.

A composition of the desired linkers from the individual oligonucleotides was achieved according to the following plan:

| 5' EBI656 | PEBI643 | PEBIG60 | 3' |
|---|---|---|---|
| 3'EBI636 | P EBI646 | P EBI638 | 5' |

2 mcl (=100 pmol) of EBI656 were added to reaction mixture No. 1 and 2 mcl of EBI 638 (=100 pmol) were added to reaction mixture No. 2 for the annealing reaction (hybridisation of the complementary oligonucleotides with each other). Reaction mixture No. 3 already contains 2 complementary oligonucleotides (EBI 643, EBI 646). All $^3$ reaction mixtures were heated to 100° C. for 2 minutes and slowly cooled in a water bath.

The short double-stranded DNA fragments produced in reactions Nos. 1 to 3 were ligated together as follows:

10 mcl of reaction mixture No. 1 (EBI 636+ EBI 656)
10 mcl of " No. 2 (EBI 660 + EBI 638)
10 mcl of " No. 3 (EBI 643 + EBI 646)
3 mcl 10 mM ATP
1 mcl DNA ligase, Boehringer Mannheim, 7 Units/mcl
The reaction lasted for 15 hours at 4° C.

The DNA was separated according to size on 1% agarose gel and the desired DNA fragment of formula XI 128 bp long was eluted from the gel (G. M. Dretzen et al., Anal. Biochem. 112. 295–298, 1981).

EXAMPLE 12

Construction of the expression vectors containing the leader DNA sequence

Plasmid HSOD6 was doubly digested with XhoI and XbaI (5 units/mcg of DNA) in CORE buffer in the usual way and the 128 bp long linker (XhoI - mitochondrial leader - XbaI) was inserted therein by known methods (pEO22-A). The hMn-SOD gene now provided with the mitochrondrial yeast leader DNA sequence was doubly digested with XhoI - EcoRI (5 units per mcg of DNA) in the CORE buffer and inserted via XhoI - EcoRI, in pKH1 (Example 6b, FIG. 8) (pEO23-A).

The expression cassette thus prepared was inserted, analogously to Example 8, via BglII/HindIII (after double digestion of the plasmids in CORE buffer and isolation of the expression cassette cut out) into the correspondingly prepared yeast transformation vector YEp13, pJDB207 and pEAS102 via the cutting sites BamHI and HindIII. Table II which follows denotes the plasmids thus obtained.

TABLE 2

Titles of the expression vectors

| Vector | Name of plasmid |
|---|---|
| pJDB207 | pEO24-AB |
| pEAS102 | pEO25-AC |
| YEp13 | pEO26-AD |

EXAMPLE 13

Yeast transformation and expression in yeast

The yeast strain WS30-5g (Example 9) was transformed with the plasmids listed in Table 2 and the transformants were tested for their expression (Example 10).

For fermentation of the transformed yeast strain WS30-5g a pre-culture having the following composition was cultivated with a magnetic stirrer and with aeration, until an optical density $OD_{546}=0.01$ was achieved: 6.7 g/l yeast nitrogen base w/o amino acids (Difco), 10 g/l glucose, 0.16 g/l arginine, 0.25 g/l lysine, 0.06 g/l tryptophan, 0.08 g/l methionine, 0.03 g/l cysteine, 0.10 g/l histidine, 0.16 g/l tyrosine, 0.17 g/l phenylalanine, 0.16 g/l threonine, 0.18 g/l isoleucine, 0.21 g/l valine, 0.40 g/l glutamic acid, 0.21 g/l glycine, 0.02 g/l of cystine, 0.15 g/l alanine, 0.20 g/l asparaginic acid, 0.20 g/l proline, 0.15 g/l serine, 0.10 g/l asparagine, 0.20 g/l glutamine, 25 mg/l adenine, 50 mg/l uracil.

The subsequent main culture having the composition: 8.0 g/l $(NH_4)_2 SO_4$, 2.56 g/l $(NH_4)_2HPO_4$, 1.16 g/l KCl, 0.60 g/l $MgSO_4 \cdot 7 H_2O$, 0.56 g/l $CaCl_2 \cdot 2H_2O$, 0.04 mg/l biotin, 80 mg/l m-inositol, 40 mg/l Capantothenate, 8 mg/l thiamine, 2 mg/l pyridoxine, 3.1 mg/l $CuSO_4 \cdot 5 H_2O$, 19 mg/l $FeCl_3 \cdot 6 H_2O$, 12 mg/l $ZnSO_4 \cdot 7 H_2O$, 14 mg/l $MnSO_4 \cdot H_2O$, 5 mg/l $H_3BO_3$, 1 mg/l KI, 2 mg/l $Na_2MoO_4 \cdot 2H_2O$, 1 g/l yeast extract, 0.2 g/l uracil, 0.1 g/l adenine, 0.5 g/l citric acid, 15 g/l glutamic acid, 0.2 g/l histidine, 0.5 g/l tryptophan, 100 g/l glucose was produced in the 20l fermenter (CHEMAP). For this purpose, 5% of the quantity of pre-culture was used as the inoculum and cultivation was effected with stirring (1000 rpm), aeration (0.5 vvm) and at a constant pH (5.0) at 28° C. in a 20l fermenter.

After the glucose content had fallen to 50 g/l, a further 50 g/l of glucose were added and fermentation was continued until the glucose content was 10 g/l (which happened after 45 hours). The fermentation liquor was then cooled, centrifuged and the biomass was frozen. The yield of biomass was 18 g/l of the wet cell weight.

The expression of the plasmid pE024-AB, pEO25-AC and pEO26-AD in yeast strain WS30-5g is documented in FIG. 12.

EXAMPLE 14

Yeast mitochondria preparation

In order to determine whether the insertion of the yeast mitochrondrial leader sequence before the hMn-SOD gene causes the protein to be imported into the mitochondria, yeast mitochondria were prepared and the Mn-SOD activity in the mitochondria and in the cytoplasm was analysed.

Yeast mitochondria were prepared by a modified form of the method of G. Daum et al., Journal Biol. Chem., 257, 13028–13033, 1982. A pre-culture of the transformants in SC-Leu liquid medium (Example 10) was cultivated by shaking (300 rpm) at 28° C. overnight. 25 ml were inoculated into 225 ml of YPD medium and cultivated overnight, like the pre-culture. The cells were generally measured at an optical density of 5–7 at 600 nm and harvested by centrifuging (Sorval, 6500 rpm, 5 min.). The cells were washed once with 100 ml of water. The cell pellet was suspended in 1M mannitol, 20 mM $KP_i$ ($KH_2PO_4/K_2HPO_4$) pH 7.4 (1 ml per 300 mg of cell weight) and 1 mg/ml of zymolase (Miles, MW 500) was added. Spheroplasts were produced by slowly shaking for 2 hours (50 rpm) at 28° C.

The spheroplasts were harvested by centrifuging (3000 rpm, 5 min., Hereaus Christ Bench Centrifuge) and washed once with 1M mannitol, 20 mM $KP_i$ pH 7.4, 1 mM PMSF (phenylmethylsulphonylfluoride). The supernatant was discarded and 1 to 2 pellet volumes of glass beads (diameter 0.1 mm) were added.

The cells were broken up by stirring for 1 minute and suspended in 2.5 ml of 0.65M mannitol, 1 mM EDTA, 1 mM PMSF. Whole cells and cell debris were centrifuged at 2000 rpm for 5 minutes (Hereaus Christ Bench Centrifuge). The mitochondria were then obtained from the supernatant by centrifuging (Sorval, J-21, 12000 rpm, 10 min.). The supernatant contains the cytoplasm and was removed in order to be investigated later for hMn-SOD activity. The reddish-brown mitochondria pellet was washed with the above-mentioned buffer (white cytoplasmic constituents were rinsed away) and the mitochondria were suspended in 2.5 ml of the same buffer. Any impurities were removed by centrifuging again (Hereaus Christ, Bench Centrifuge, 4000 rpm, 5 min.) and the mitochondria were pelleted from the supernatant in a second centrifugation (Sorval J-21, 12000 rpm, 10 min.). The mitochondria were broken up with glass beads, in a manner similar to the method for breaking up yeast cells (van Loon et al., Proc.Natl. Acad.Sci. USA 83, 3820–3824, 1986) and tested for their content of Mn-SOD in activity gel (FIG. 13).

EXAMPLE 15

Purification of the hMn-SOD according to the invention

The recombinant hMn-SOD was isolated from the strain WS30-5g/pEO24-AB (yeast vector pJDB207) via several steps.

Step 1: Cell disintegration

The cell mass (Example 13) was washed in 10 ml of distilled water per gram of wet weight and centrifuged for 15 minutes at 16000×g. The precipitate was resuspended in Na, K-phosphate buffer (50 mM, pH 7.0) in the ratio 1:3 (w/v). The cells were then broken up in a continuously operating cell mill (Dynomill KDL; Bachofer, Basel, Switzerland; 0.6 l grinding container, water-cooled) using glass beads (0.1 mm in diameter) at a flow rate of 6 liters per hour. The cell extract was centrifuged for 15 minutes (16000×g, 4° C.) and the precipitate was discarded.

Step 2: Polyethyleneimine precipitation

A 5% (w/v) aqueous polyethyleneimine solution (pH 8.0) was added with stirring to the supernatant from step 1 until a final concentration of 0.5% was achieved (polyethyleneimine, Serva, Heidelberg). The mixture was then stirred for a further 30 minutes and the precipitate was centrifuged off at 16000×g (30 minutes).

Step 3: Heat precipitation

The supernatant from step 2 was heated in steel beakers with stirring in a hot water bath (80° C.) to 60° C. and cooled to room temperature again in an ice bath. Any protein precipitated was removed by centrifuging (10,000×g, 10 min., 4° C.).

Step 4: Ammonium sulphate precipitation

The supernatant from step 3 was brought to 20% saturation with solid ammonium sulphate and the precipitate was removed by centrifuging (10,000×g, 15 min., 4° C.). The ammonium sulphate concentration was then increased to 90% and the precipitate was obtained by centrifuging (10,000×g, 15 min., 4° C.). The sediment was taken up in a little MES buffer (morpholino ethanesulphonate buffer, 50 mM, pH 6.0; 2-morpholino ethanesulphonic acid of Sigma, Deisenhofen) and dialysed overnight against the same buffer.

Step 5: Cation exchange chromatography

A Mono S column (Mono S HR 5/5, Pharmacia, Sweden) was equilibrated with 5 column volumes of MES buffer. After the column had been charged with the extract from step 4, any unbound proteins were washed away with 5 column volumes of MES buffer. The hMn-SOD according to the invention was then eluted in a linear gradient of 0–50 mM NaCl in MES buffer (20 column volumes). Fractions which contained Mn-SOD activity were combined and dialysed against Na, K phosphate buffer (5 mM, pH 7.0).

Figure 14:
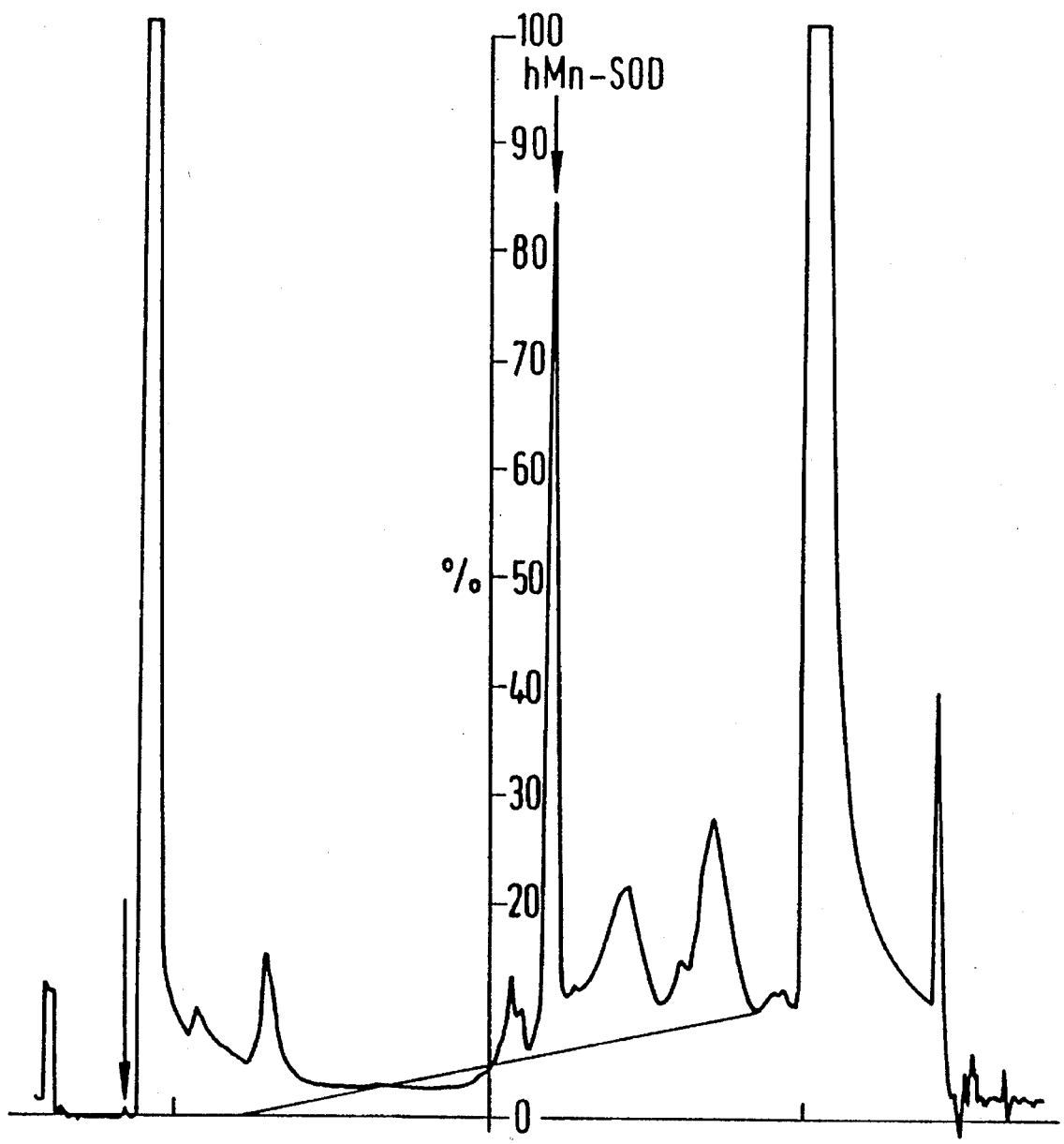

The native yeast SOD enzymes (Mn-SOD, CuZn-SOD) can be separated off in this purification step. FIG. 14 shows an elution diagram.

Step 6: Adsorption chromatography on hydroxylapatite.

A hydroxylapatite column (HA Ultrogel, IBF, Villeneuvela-Garenne, France) equilibrated with phosphate buffer (5 mM, pH 7.0) was charged with the dialysate from step 5 and the hMn-SOD according to the invention was eluted with a linear gradient (20 column volumes) of 5–300 mM of Na, K-phosphate, pH 7.0.

The degree of purity of hMn-SOD achieved in the individual purification steps was monitored by reductive SDS-polyacrylamide gel electrophoresis (FIG. 15).

EXAMPLE 16

Characterisation of the hMn-SOD according to the invention

The hMn-SOD according to the invention, purified as in Example 15, was analysed by gel permeation HPLC, reverse phase HPLC, N-terminal sequencing, SDS-gel electrophoresis, native gel electrophoresis and isoelectric focusing and compared with natural hMn-SOD.

a. Gel permeation HPLC:

Column: Water protein pack I 125, 2×(7.8×300 mm), 10 mcm particle diameter

Eluant: 0.5M $Na_2SO_4$, 0.02M $NaH_2PO_4$, pH 7.0, 0.04% Tween 20, 25% propyleneglycol Flux: 0.5 ml/min Detection: UV absorption, 214 nm Natural hMn-SOD or hMn-SOD according to the invention show the main peak of the SOD tetramer at a molecular weight of 70,000 and 76,000, respectively, calibration being effected by means of four standard proteins. Within the experimental degree of error of this method, these values can be regarded as identical.

b. Reverse phase HPLC

Column: Bakerbond WP $C_{18}$, 4.6×250 nm, 5 mcm particle diameter, 30 nm pore diameter Eluant A: 0.1% trifluoroacetic acid in water Eluant B: 0.1% trifluoroacetic acid in acetonitrile Gradient: 20% B for 2 min., 20–68% B in 24 min, 68% B for 10 min., 68–20% B in 1 min Flux: 1.0 ml/min Detection: UV absorption, 214 nm and 280 nm Both natural hMn-SOD and hMn-SOD according to the invention show a retention time of just 21 minutes (20.7 and 20.9 min respectively).

c. N-terminal sequencing

A peak of hMn-SOD according to the invention, desalinated by reverse phase HPLC, was sequenced. Sequencing was carried out using a gas phase sequenator made by Applied Biosystems (Model 470 A) with the program 02RPTH. With an initial quantity of 0.8 nM, it was possible to sequence up to amino acid 20. 100% agreement was found with the expected sequence (of natural protein and cDNA). The leader sequence for transporting into the mitochondria had been split off completely.

d. SDS gel electrophoresis

Separating gel: 15% acrylamide

Stacking gel: 4% acrylamide

Staining: silver staining according to B. R. Oakley et al. (Analyt. Biochem. 105, 361–363, 1980).

Gel measurements: 0.75 mm (8×10 cm)

Running conditions: 60 min, 150 V

The SDS gel electrophoresis was carried out substantially according to the method originally described by U.K. Lammli (Nature 2? 7, 680–685, 1970). In the preparation of the samples for hMn-SOD, the samples were mixed with DTT as the reducing agent and boiled. hMn-SOD occurred on the SDS gel mainly as a monomer with M approximately 25,000. Depending on the completeness of the reduction, the tetramer with M approximately 90,000 can also be detected. FIG. 15 shows a 15% SDS polyacrylamide gel after silver staining.

e. Native gel electrophoresis

Separating gel: 7.5% native PAGE according to Davis, B. J. (Ann. NY Acad. Sci. 121, 404–427, 1964)

Stacking gel: 2% acrylamide+sucrose

Gel dimensions: 0.75 mm (8×10 cm)

Running conditions: 75 min, 150 V (const.)

Staining: Coomassie Blue by known methods and activity staining with o-dianisidine according to Misra, H. P., Fridovich, I. (Arch. Biochem. Biophys. 183, 511–515, 1977)

The hMn-SOD according to the invention obtained after hydroxylapatite chromatography showed a uniform band located in the same position after electrophoresis, both with Coomassie Blue staining (quantity of hMn-SOD applied: 0.3 mcg) and also after activity staining with o-dianisidine (quantity of hMn-SOD applied: 75, 30 or 15 ng).

f. Isoelectric focusing pH range: 3.5–9.5

Gel plates: LKB, PAG plate (1 mm×(9×10 cm))

Electrode solutions: 1M phosphoric acid (anode) 1M sodium hydroxide solution (cathode)

Cooling temperature: 7° C.

Quantity of sample: 4.0 or 6.5 mcg

Running conditions: pre-focusing 500 Vh focusing 3000 Vh in all

Staining: Coomassie Blue, activity staining with o-dianisidine pI=8.15 was determined as the isoelectric point.

We claim:

1. A method for the preparation of tetrameric human manganese superoxide dismutase (hMn-SOD) consisting of 198 amino acids, comprising (a) obtaining a yeast host transformed with a yeast expression vector comprising a cloned gene encoding hMn-SOD consisting of 198 amino acids;

(b) cultivating said yeast host under conditions which result in the expression of tetrameric hMn-SOD: and (c) isolating said tetrameric hMn-SOD.

2. The method of claim 1, wherein said yeast expression vector further comprises a mitochondrial leader or signal DNA sequence positioned directly after the start codon (ATG) of the hMn-SOD gene and before the first codon coding for hMn-SOD.

* * * * *